United States Patent [19]

Marshall et al.

[11] Patent Number: 4,820,723

[45] Date of Patent: Apr. 11, 1989

[54] DISUBSTITUTED TETRAZOLE LEUKOTRIENE ANTAGONISTS AND METHODS FOR THEIR USE THEREAS

[75] Inventors: Winston S. Marshall, Bargersville; Sandra K. Sigmund, Carmel; Celia A. Whitesitt, Greenwood, all of Ind.

[73] Assignee: Eli Lilly and Company, Indianapolis, Ind.

[21] Appl. No.: 85,588

[22] Filed: Aug. 14, 1987

[51] Int. Cl.$^4$ ............... C07D 257/04; C07D 403/06; A61K 31/41
[52] U.S. Cl. .................................. 514/381; 548/252; 548/253
[58] Field of Search ................. 548/252, 253; 514/381

[56] References Cited

U.S. PATENT DOCUMENTS 4,661,505  4/1987  Marshall et al. ............... 514/381
4,663,332  5/1987  Carson et al. ................. 514/340

Primary Examiner—David B. Springer
Attorney, Agent, or Firm—Robert A. Conrad; Leroy Whitaker

[57] ABSTRACT

The instant invention provides disubstituted tetrazoles that antagonizes the effect of leukotrienes $C_4$, $D_4$ or $E_4$ or any combination thereof in selected tissues. The disubstituted tetrazoles are used in pharmaceutical formulations and methods of treatment of conditions caused by excessive release or production of leukotrienes $C_4$, $D_4$ or $E_4$ or any combination thereof. Such conditions include an immediate hypersensitivity reaction of the type represented by asthma, or by shock or other adverse cardiovascular effects.

42 Claims, No Drawings

DISUBSTITUTED TETRAZOLE LEUKOTRIENE ANTAGONISTS AND METHODS FOR THEIR USE THEREAS

BACKGROUND OF THE INVENTION

Research in the area of allergic reactions of the lung has provided evidence that arachidonic acid derivatives formed by the action of lipoxygenases are related to various disease states. Some of these arachidonic acid metabolites have been classified as members of a family of eicosatetraenoic acids termed leukotrienes. Three of these substances are currently thought to be major components of what has been previously called slow reacting substance of anaphylaxis (SRS-A).

It is the object of this invention to provide novel chemical agents which are leukotriene antagonists that can be used therapeutically in the treatment of allergic disorders such as asthma, where leukotrienes are thought to be causal mediators. It is a further object of this invention to provide highly potent antagonists whose spectrum of activity is limited to leukotrienes $LTC_4$, $LTD_4$ and $LTE_4$.

SUMMARY OF THE INVENTION

This invention provides for final products of the Formula I

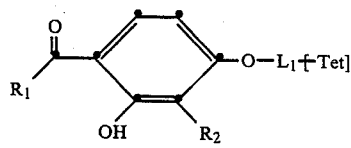

or a pharmaceutically-acceptable base addition salt thereof wherein $R_1$, $R_2$, $L_1$ and [Tet] are as defined below.

Another aspect of the invention is intermediate compounds of the Formula II

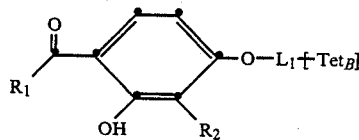

$R_1$, $R_2$, $L_1$ and [$Tet_B$] are as defined below, or a pharmaceutically-acceptable base addition salt thereof;

As the instant final products are therapeutic agents, the invention also provides for pharmaceutical compositions (comprised of a therapeutically-effective amount of the compounds of claim 1 and a pharmaceutically-acceptable carrier). Also provided are methods of use for treating immediate-hypersensitivity type asthma and, in general, diseases caused by the release or production of an excessive amount of leukotrienes $C_4$, $D_4$, or $E_4$ or any combination thereof in a mammal (both of which methods comprise administering to said mammal a leukotriene $C_4$, $D_4$, or $E_4$ antagonizing amount of the compounds of Formula I)

DETAILED DESCRIPTION OF THE INVENTION

One aspect of the present invention is the leukotriene $C_4$, $D_4$ and $E_4$ antagonist compounds of the Formula I:

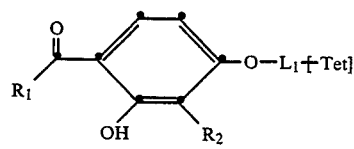

wherein:
$R_1$ is $C_1$ to $C_8$ alkyl or phenyl;
$R_2$ is $C_2$ to $C_8$ alkyl or $C_3$ to $C_6$ alkenyl;
$L_1$ is $C_3$ to $C_{10}$ alkylidene or phenyl;
[Tet] is a disubstituted 1H- or 2H-tetrazolyl ring of the formula:

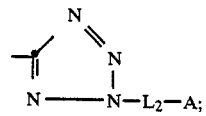

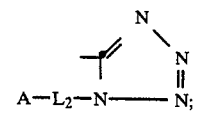

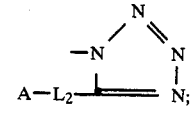

or

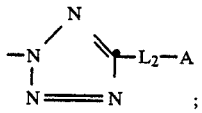

$L_2$ is
(1) a $C_1$ to $C_{10}$ alkylidene group; or
(2) a benzyl group of the formula:

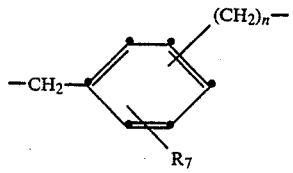

wherein $R_7$ is a hydrogen atom, a hydroxy group, or acetoxy; and n is from 0 to 3 (and the single methylene group is also bonded to the tetrazolyl ring of [Tet]);
A is
(1) a group of the formula —COOH; or
(2) a 5-(tetrazolyl) group; with the proviso that when $L_1$ is phenyl, —$L_2$—A is not bonded to the 5-position of [Tet]tetrazolyl ring;
or a pharmaceutically-acceptable salt thereof.

In Formula I, the term "$C_1$ to $C_8$ alkyl" refers to the straight and branched aliphatic radicals of 1 to 8 carbon atoms such as methyl, ethyl, propyl, isopropyl, butyl, isobutyl, sec-butyl, tert-butyl, amyl, isoamyl, sec-amyl, 1,2-dimethylpropyl, tert-amyl (1,1-dimethylpropyl), hexyl, isohexyl (4-methylpentyl), sec-hexyl (1-methylpentyl), 2-methylpentyl, 3-methylpentyl, 1,1-dimethylbutyl, 2,2-dimethylbutyl, 3,3-dimethylbutyl, 1,2-dimethylbutyl, 1,3-dimethylbutyl, 1,2,2-trimethylpropyl, 1,1,2-trimethylpropyl, n-heptyl, n-octyl, 2-methylhexyl, 3,4-dimethylpentyl, 4-ethylpentyl, 3,3-dimethylpentyl, 3-(isopropyl)pentyl, 4-methylheptyl, 2,4-dimethylpentyl, and the like. The term "$C_1$ to $C_8$ alkyl" includes within its definition the definition of the term "$C_2$ to $C_2$ alkyl".

The term "$C_3$—$C_6$ alkenyl" refers to straight and branched radicals of three to six carbon atoms such as allyl, isopropenyl, butenyl, isobutenyl, 3-methyl-2-butenyl, n-hexenyl, and the like.

The term "$C_1$ to $C_{10}$ alkylidene" refers to straight or branched divalent hydrocarbon chains such as —$CH_2$—, —$CH(CH_3)$—, —$C(CH_3)_2$—, —$CH(C_2H_5)$—, —$CH_2CH_2$—, —$CH_2CH(CH_3)$—, —$CH(CH_3)CH_2$—, —$CH(CH_3)CH(CH_3)$—, —$CH_2C(CH_3)_2$—, —$CH_2CH(C_2H_5)$—, —$CH_2CH_2CH_2$—, —$CH(CH_3)CH_2CH_2$—, —$CH_2CH(CH_3)CH_2$—, —$CH_2CH(C_2H_5)$—, —$CH_2CH_2CH(C_2H_5)$—, —$C(CH_3)_2CH_2CH_2$—, —$CH(CH_3)CH_2CH(CH_3)$—, —$CH_2CH_2CH_2CH_2$—, —$CH_2C(CH_3)_2CH_2CH_2$—, —$CH_2C(CH_3)_2CH_2$—, —$CH_2CH_2CH(C_2H_5)CH_2$—, —$CH_2CH_2CH_2CH_2CH_2$—, —$CH(CH_3)CH_2CH_2CH_2CH_2$—, —$CH_2CH_2CH_2CH_2CH_2CH_2$—, —$(CH_2)_7$—, —$(CH_2)_8$—, —$(CH_2)_9$—, —$(CH_2)_{10}$—, —$CH_2$—$CH(CH_3)$—$(CH_2)_4$—, —$(CH_2)_2$—$CH(C_2H_5)$—$(CH_2)_3$—, —$CH_2$—$CH(CH_3)$—$(CH_2)_2$—$CH(C_2H_5)$—$(CH_2)_2$, and the like. The term "$C_1$ to $C_{10}$ alkylidene" includes the definition of straight chain and branched alkylidene groups of the term "$C_3$ to $C_{10}$ alkylidene".

The pharmaceutically-acceptable salts of this aspect of the invention include salts derived from inorganic bases, such as ammonium and alkali and alkaline earth metal hydroxides, carbonates, bicarbonates, and the like, as well as salts derived from basic organic amines, such as aliphatic and aromatic amines, aliphatic diamines, hydroxy alkylamines, and the like. Such bases useful in preparing the salts of this invention thus include ammonium hydroxide, potassium carbonate, sodium bicarbonate, calcium hydroxide, sodium hydroxide, methylamine, diethylamine, ethylenediamine, cyclohexylamine, ethanolamine, and the like. The potassium and sodium salt forms are particularly preferred, with the sodium salt form being the most preferred.

Those skilled in the art will recognize that, when alkyl or alkylidene groups are branched, various stereoisomers will exist. This invention is not limited to any particular stereoisomer but includes all possible individual isomers and racemates of the compounds of Formula I and Formula II. Similarly, when an alkene group is present, both the individual cis and trans isomers and their mixture are included as part of this invention.

A preferred group of the final product compounds of Formula 1 is composed of compounds wherein [Tet] is a disubstituted 2H-tetrazolyl ring of the formula:

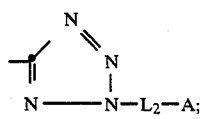

-continued
or

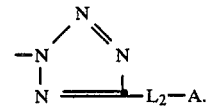

Within the generally preferred group of (internal) 5-(2H-tetrazolyl) compounds are the preferred 5-(2H-tetrazolyl) compounds, wherein $R_1$ is methyl, $R_2$ is n-propyl, and $L_1$ is n-($C_3$ to $C_6$) alkyl.

The preferred 5-(2H-tetrazolyl) compounds contain two groups of compounds of special importance: the first group wherein $L_1$ is n-butyl bonded to the 5-position of the internal 2H-tetrazolyl ring, and the second group when $L_1$ is again n-butyl but is bonded to the 2 (N-2) position of the internal 2H-tetrazolyl ring. The two groups of special importance will be referred to for convenience sake as the 5-($L_1$)-2H-tetrazolyl products and the 2-($L_1$)-2H-tetrazolyl products, respectively.

Preferred 5-($L_1$)-2H-tetrazolyl products occur when the external linking group $L_2$ is n-($C_3$ to $C_6$) alkyl or a substituted benzyl group of the formula

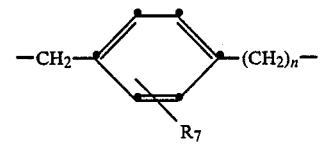

wherein n is 0 or 1.

The preferred 5-($L_1$)-2H-tetrazolyl products contain three further preferred groups; the first further group sets A as 5-tetrazolyl and the external linking group $L_2$ as n-($C_3$ to $C_5$) alkyl (referred to herein as the "bis(tetrazole)compounds"); the second sets group A as carboxy and $L_2$ is again designated as straight-chain $C_3$ to $C_5$ alkyl (herein referred as the "carboxy alkyltetrazoles"); the third group again has A as carboxy but $L_2$ is a benzyl group of the formula

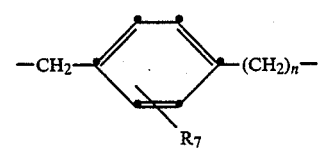

wherein n is 0 or 1 (referred to herein as the "carboxybenzyl tetrazoles").

Among the bis(tetrazole) products is an especially preferred compound of the Formula III:

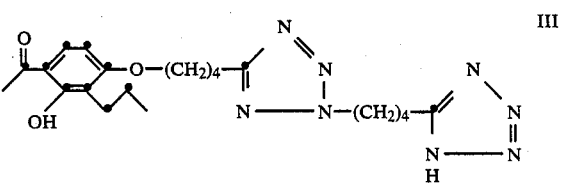

(and the corresponding 2-H isomer of the external tetrazole). The sodium salt of the compound of Formula III is also an especially preferred product. The other especially preferred compound of the bis(tetrazole)

compounds has $L_2$ as a straight-chain $C_3$ alkyl (i.e., n-propyl) group.

The carboxyalkyl tetrazole group of products contain two especially preferred products; those products set $L_2$ as either n-propyl or n-pentyl.

The carboxybenzyl tetrazoles encompass an especially preferred product wherein n is 0, $R_7$ is a hydrogen atom and the substitution pattern of the phenyl ring is in the para configuration, that is, a compound of the Formula IV:

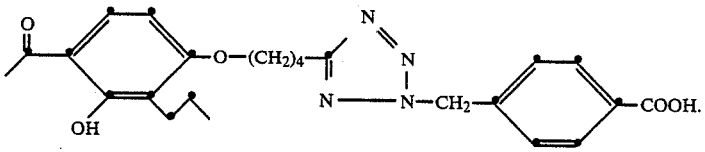

IV

An especially preferred form of the product of Formula IV is the sodium salt thereof.

The other (more preferred) subgroup of preferred 2H-tetrazolyl products (i.e., the 2-($L_1$)-2H-tetrazolyl products) contains a preferred group of products. This preferred group sets $L_1$ as n-butyl, and more importantly, has the external linking group $L_2$ as either an n-($C_3$ to $C_5$) alkyl or a benzyl group of the formula

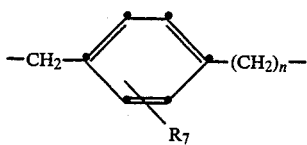

wherein n is 0 and $R_7$ is a hydrogen atom. Two especially preferred products within this latter group set A as carboxy and $L_2$ as n-propyl and when, A and $L_2$ are taken together, a group of the formula

(i.e., n is zero with para substitution on the ring).

Another aspect of the invention are intermediates of Formula II

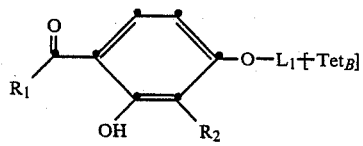

II wherein:
$R_1$ is $C_1$ to $C_8$ alkyl or phenyl;
$R_2$ is $C_2$ to $C_8$ alkyl or $C_3$ to $C_6$ alkenyl;
$L_1$ is $C_3$ to $C_{10}$ alkylidene or phenyl;
[$Tet_B$] is a disubstituted 1H- or 2H-tetrazolyl ring of the formula:

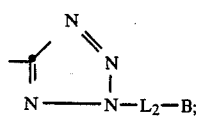

-continued

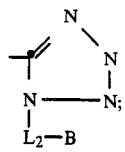

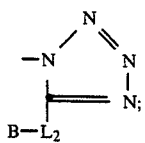

or

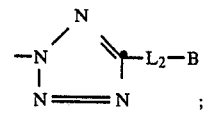

wherein:
$L_2$ is
(1) a $C_1$ to $C_{10}$ alkylidene group; or
(2) a benzyl group of the formula:

wherein $R_7$ is an acetoxy group or a protected hydroxy group, and
n is from 0 to 3; (and the single methylene group is bonded to the [$Tet_B$]tetrazolyl ring); and
B is
(1) a group of the formula

—$COOR_8$ wherein $R_8$ is ethyl or a carboxy-protecting group;
(2) cyano; or
(3) halo;
with the proviso that when $L_1$ is phenyl, —$L_2$—B is not bonded to the 5-position of the [$Tet_B$]tetrazolyl ring.

In the above Formula II, the terms "$C_1$ to $C_8$ alkyl", "$C_2$ to $C_8$ alkyl", "$C_3$ to $C_6$ alkenyl", "$C_3$ to $C_{10}$ alkylidene" and "$C_1$ to $C_{10}$ alkylidene" are as defined for Formula I. The term "halo" means chloro, bromo or iodo.

In Formula II, the term "carboxy-protecting group" refers to one of the carboxylic acid substituents commonly employed to block or protect the carboxylic acid functionality while reacting other functional groups on the compound. Examples of such carboxylic acid protecting groups include tert-butyl, 4-methoxybenzyl, benzhydryl (diphenylmethyl), benzyl, paranitrobenzyl, 2,4,6-trimethoxybenzyl, trityl, 4-methoxytrityl, 4,4'-dimethoxytrityl, and 4,4',4''-trimethoxytrityl and like moieties. The species of carboxy-protecting group employed is not critical so long as the derivatized carboxylic acid is stable to the condition of subsequent reaction(s) (such as alkylation) on other positions of the intermediates of Formula II and can be removed at the appropriate point without disrupting the remainder of the molecule. Preferred carboxylic acid protecting groups include benzyl, benzhydryl (diphenylmethyl), para-nitrobenzyl and 4-methoxybenzyl, with the more preferred groups being benzhydryl and para-nitrobenzyl. Similar carboxy-protecting groups used in the heterocyclic art are similarly embraced by the above terms. Further examples of these groups are found in E. Haslam in "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981, Chapter 5.

Similarly, the term "hydroxy-protecting group" or "protected hydroxy" refers to readily cleavable groups bonded to hydroxyl groups such as the formyl group, the chloroacetoxy group, the benzhydryl group, the trityl group, the p-nitrobenzyl group, the trimethylsilyl group and the like. Further examples of groups referred to by the above terms are described by C. B. Reese and E. Haslam in "Protective Groups in Organic Chemistry", J. G. W. McOmie, Ed., Plenum Press, New York, N.Y., 1973, Chapters 3 and 4, respectively, and T. W. Greene, "Protective Groups in Organic Synthesis", John Wiley and Sons, New York, N.Y., 1981, Chapters 2 and 3.

A generally preferred group of intermediates of Formula II is composed of compounds wherein [Tet$_B$] is a disubstituted 2H-tetrazolyl ring of the formula:

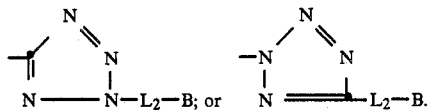

Within the generally preferred group of (internal) 5-(2H-tetrazolyl) intermediates are the preferred 5-(2H-tetrazolyl)intermediates, wherein $R_1$ is methyl, $R_2$ is n-propyl and $L_1$ is straight-chain $C_3$ to $C_6$ alkyl.

The preferred 5-(2H-tetrazolyl)intermediates contain two groups of intermediates of special importance (teaching those of the final products), thus: a group wherein $L_1$ is an n-butyl group bonded to the 5-position of the internal 5-(2H-tetrazolyl) ring, and a second group when $L_1$ again is n-butyl but 0 is bonded to the 2 (i.e., N-2) position of the internal 5-(2H-tetrazolyl) ring. The two groups of special importance are also referred to in this application as the 5-($L_1$)-5-(2H-tetrazolyl) intermediates and the 2-($L_1$)-5-(2H-tetrazolyl) intermediates, respectively.

Preferred 5-($L_1$)-5-(2H-tetrazolyl) intermediates are as follows:
(a) B is cyano and $L_2$ is n-($C_3$ to $C_6$)alkyl or a benzyl group of the formula

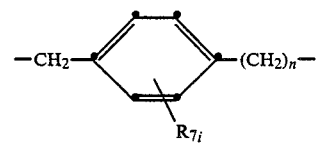

wherein
n is 0 or 1 and
$R_{7i}$ is hydrogen;
(b) B is an ethyl ester moiety and $L_2$ is (1) n-($C_2$ to $C_5$)alkyl or (2) a benzyl group of the formula

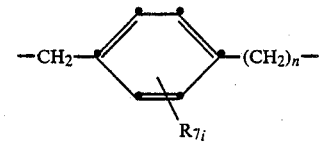

wherein
$R_{7i}$ is ortho or meta acetoxy and
n is 0; or
(c) B is bromo and $L_2$ is a benzyl group of the formula

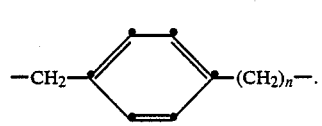

Among the preferred 5-($L_1$)-5-(2H-tetrazolyl) intermediates are two groups of more preferred intermediates. One of these groups sets $L_2$ as a benzyl group, n as zero, B as cyano, and has meta or para substitution, in other words meta- or para-toluylnitrile; the other group also has B as cyano and $L_2$ as either n-($C_3$ to $C_5$) alkyl or a benzyl group of the formula

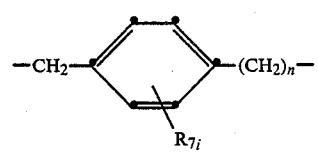

wherein $R_{7i}$ is a hydrogen atom and n is 0 or 1.

A most preferred group of intermediates within the latter group of more preferred intermediates has $L_2$ as n-butyl.

Similarly, within the preferred 2-($L_1$)-5-(2H-tetrazolyl) intermediates are a more preferred group that equates B with the ethyl ester (i.e., B=COOR$_8$ wherein R$_8$ is ethyl) and $L_2$ as either n-($C_3$ to $C_5$) alkyl or a benzyl group of the formula

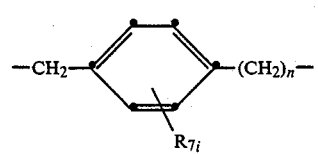

wherein n is 0 or 1 and $R_{7i}$ is a hydrogen atom. The most preferred compounds in this more preferred group have the exterior linking group $L_2$ as n-propyl or a benzyl group of the formula

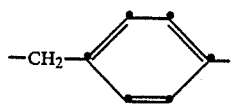

(i.e., n is zero and $R_{7i}$ is a hydrogen atom).

As will be discussed more fully below, further aspects of the instant invention are pharmaceutical formulations and methods of use employing the final products of Formula I.

Specifically, the invention includes pharmaceutical formulations, which comprise a therapeutically-effective amount of the compounds of Formula I, the preferred compounds of Formula I (as defined above and in claim 2), the compound of Formula III, and the sodium salt of the compound of Formula III.

The invention provides a method of treating a mammal suffering from or susceptible to any condition characterized by an excessive release of either leukotriene $C_4$, $D_4$, or $E_4$ (or any combination thereof). The method comprises administering to the mammal a leukotriene-antagonizing amount of the products of Formula I, the preferred products of Formula I (as defined above and in claim 2), the compounds of Formula III above (or a pharmaceutically acceptable salt thereof) or the sodium salt of the compound of Formula III.

Finally, the invention provides a method of treating a mammal suffering from or susceptible to an immediate hypersensitivity reaction of the type represented by asthma. The method comprises administering to said mammal a therapeutically-effective amount of a product of Formula I, a preferred product of Formula I, a product of the Formula III (or a pharmaceutically acceptable salt thereof) or the sodium salt of the product of Formula III.

The final products (Formula 1) are synthesized from the instant intermediates (Formula II) by methods well known in the art. For example, when B in Formula II is halo, the intermediate can be converted to the cyano intermediate (B =cyano) which in turn can be converted to either the 5-tetrazolyl or carboxy (A is 5-tetrazolyl or carboxy, respectively) final products. Thus, the halo intermediate can be reacted with a source of nucleophilic cyanide anion under $S_n2$ conditions. Typically, sodium or potassium cyanide (usually in slight excess) is reacted with the halo intermediate in a polar, aprotic solvent (such as dimethylsulfoxide or N,N-dimethylformamide) at preferably elevated temperatures (50° C. to the reflux temperature of mixture, although room temperature is also acceptable).

The cyano intermediate of Formula II (B is cyano) can be converted to either the 5-(tetrazolyl) final product (A is 5-(tetrazolyl), as either the 1H- or 2H- isomer or a mixture) or the carboxy final products (or the salts thereof) by methods known in the art. Thus, the cyano intermediates can be treated with an alkali metal azide such as sodium azide, ammonium chloride, and (optionally) lithium chloride in a nonreactive high-boiling solvent such as N,N-dimethylformamide (DMF), preferably at temperatures from about 60° C. to about 125° C. Alternatively, tris(n-butyl)tin azide or tetramethylguanidinium azide, in a solvent such as tetrahydrofuran, dimethoxyethane, diethoxyethane, or the like, may be used in place of the alkali metal azide, ammonium chloride, lithium chloride and DMF.

As indicated above, one method of synthesizing the carboxy final product (Formula I, A =carboxy) is to hydrolyze the cyano intermediates. The hydrolysis generally involves heating the cyano derivative in aqueous alcohol in the presence of a base such as sodium or potassium hydroxide. Another method of synthesizing the carboxy final products is to hydrolyze the ester intermediate (Formula 11, B is a group of the formula —COOR$_8$). For example, when $R_8$ is ethyl, the ethyl ester intermediate is treated with aqueous sodium or potassium hydroxide solution at room temperature or a high temperature (such as 50° C. to the reflux temperature of the mixture). The free acid final product can be isolated by acidifying the (cooled) reaction mixture. If $R_8$ is a carboxy-protecting group, the group is removed by methods well known in the art. Thus, the benzhydryl ester can be removed by stirring (and optionally heating) the ester in a strong organic acid such as trifluoroacetic acid or acetic acid. The salts of the carboxy final products are made by reacting the free acid with the appropriate base in the normal manner.

The desired products from the above reactions can be isolated by conventional means, and preferably by chromatography. Column chromatography is a preferred method, and high pressure column chromatography over silica offers a most efficient way of purifying the final products.

The intermediates of Formula II are made by a variety of methods. For convenience sake the following synthetic discussion will be divided according to the two broad types of substitution pattern of the internal tetrazole. Thus, the first class of reactions ("Class 1 reactions") synthesize intermediates wherein [Tet$_B$](the internal tetrazole) is bonded to the internal linking group at the 5 position and is of the formula:

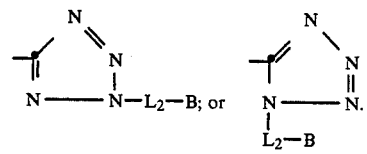

The second class of reactions ("Class 2") synthesizes intermediates where [Tet] has the opposite configuration and is of the formula:

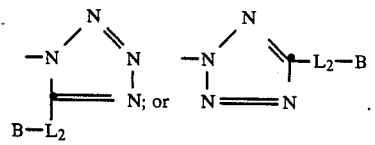

There are two major Class 1 reactions; one involves alkylating the internal tetrazole when the tetrazole is already a part of the rest of the molecule, the other involves assembling the internal linking group by combining two otherwise complete subunits (one containing the ketophenone and one containing the interior tetrazole ring).

The first of the Class 1 reactions, referred to here as the "core-tetrazole alkylation", is depicted below in Scheme 1:

Scheme 1

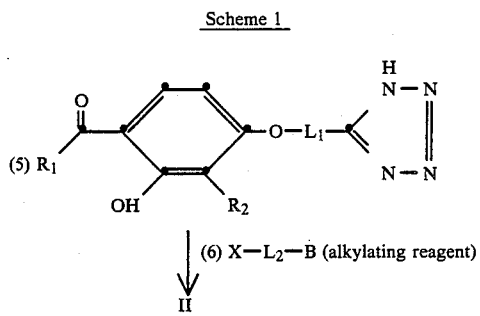

In the above Scheme, $R_1$, $R_2$, $L_1$, $L_2$, and B, are as for Formula II. "X" is a good leaving group for $S_n2$ reactions, and is preferably chloro or bromo. (Note that the tetrazole of the starting material can also be 2-H isomer, or alkali metal salt of either the 1H- or 2H-isomer.)

The reaction depicted in the above Scheme usually involves approximately equimolar amounts of the starting material and reagent, although other ratios, especially those wherein the alkylating reagent is in excess, are operative. The reaction is best carried out in a polar, aprotic solvent employing the tetrazole starting material in the presence of a base (such as an alkali metal hydroxide). Preferred reaction conditions involve employing the mono-substituted tetrazole along with potassium carbonate in a solvent such as acetone or methyl ethyl ketone, or in a mixture of acetonitrile and hexamethylphosphoramide. When the leaving group is bromo, a catalytic amount of an iodide salt, such as potassium iodide, may be added to speed the reaction. The temperature of the reaction is from about ambient temperature to about the reflux temperature of the reaction mixture. When elevated temperatures are employed, the reaction is usually complete in one to four hours.

The core tetrazole alkylation depicted in Scheme 1 affords both the N-1 and N-2 internal tetrazole isomers of the intermediates. These isomers may be separated by standard techniques at any of the intermediate stages or upon formation of the final products. Such techniques include fractional crystallization or preferably column chromatographic techniques, such as high pressure liquid chromatography.

The second of the Class 1 reactions is depicted below as Scheme 2:

Scheme 2

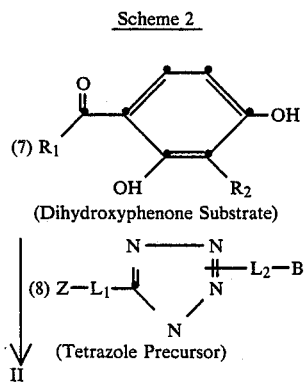

In Scheme 2, the variables $R_1$, $R_2$, and $L_2$, are the same as for Formula II. B is either cyano or a group of the formula —$COOR_8$. $L_1$ is other than phenyl. Finally, Z is a good leaving group for $S_n2$ conditions, and is especially a chloro or bromo group.

The reaction depicted in Scheme 11 above usually employs equimolar amounts of the Dihydroxyphenone Substrate and Tetrazole Precursor, although different stoichiometries are completely operative. The reaction is best carried out in nonreactive solvents such as ketones (especially acetone or methyl ethyl ketone) or in dimethylformamide in the presence of a base (preferably an alkali metal hydroxide or carbonate, and more preferably potassium carbonate). Especially when Z is chloro, a catalyst such as lithium, potassium or sodium iodide may be added to increase the reaction rate. Alternatively, ethanol and one equivalent of sodium hydroxide per equivalent of Tetrazole Precursor could be a reaction medium for Scheme 2. The reaction may be carried out at temperatures of about ambient temperature up to the boiling point of the reaction mixture, the former being preferred.

The two major types of Class 2 Reactions are set forth below as Schemes 3 and 4.

The first such reaction alkylates the internal tetrazole with the rest of the internal linking group (bonded to the ketophenone). This internal tetrazole alkylation is depicted below as Scheme 3:

Scheme 3

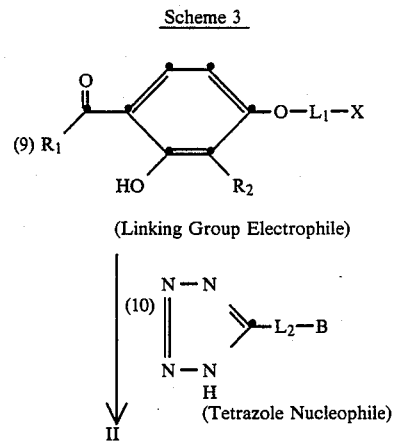

In the above Scheme 3 both the N-1 and N-2 isomers of the internal tetrazole are produced. The variable "B" is other than halo, while all the other variables used that are a part of Formula II have the same meaning as Formula 11. "X" on the Linking Group Electrophile is a good $S_n2$ leaving group, and is preferably chloro or bromo.

The alkylation of Scheme 3 can employ equimolar amounts of the Linking Group Electrophile and Tetrazole Nucleophile, although the reaction is operative using excesses of either compound. The reaction uses aprotic, polar solvents such as ketones (acetone, methyl ethylketone), and preferably methyl ethyl ketone. A weak base (such as sodium or potassium carbonate) is added in at least an equimolar amount of the Tetrazole Nucleophile. When the leaving group X is chloro or bromo, a catalytic amount of lithium, potassium or sodium iodide is preferably added. The reaction is carried out from about 25° C. to the reflux temperature of the mixture. The reaction is typically complete in two hours. The isomers of the tetrazole product are preferably separated by column chromatography over silica, and more preferably with high pressure liquid chromatography over silica. The HPLC is preferably carried out with a gradient elution of ethyl acetate in hexane plus 1% acetic acid or methanol in methylene chloride.

The second of the Class II reactions is a quite similar to the Class I set forth in Soheme 2. The analogous Class II reaction is set forth below as Scheme 4.

Scheme 4

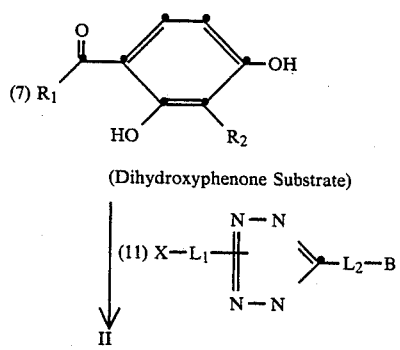

(Dihydroxyphenone Substrate)

The variables and reaction conditions for Scheme 4 are the same as those for Scheme 2.

The progress of the reactions described above for making the products and intermediates can be followed by conventional spectroscopic and chromatographic techniques. Such techniques include infrared and nuclear magnetic spectroscopy, thin layer chromatography, column chromatography and high pressure liquid chromatography. The preferred techniques are chromatographic. The reactions discussed above are stopped when the monitoring technique shows the reaction is substantially complete.

The products of the above reactions for synthesizing the final products and intermediates can be isolaed and purified by methods well known in the art. Such methods include chromatographic methods. A preferred method of isolation is high pressure liquid chromatography over a silica gel support.

Many of the reagents and starting materials in the above Schemes 1 through 4 are known in the art, and some are also commercially available. For example, many of the various precursors, starting materials and reagents are discussed in W. S. Marshall et al., U.S. Pat. No. 4,661,505, issued Apr. 28, 1987, J. Goldsworthy et al., U.S. Pat. No. 4,595,540, issued June 17, 1986, R. D. Dillard, EPO Patent Application Publication No. 132,366, published Jan. 30, 1985, P. R. Bernstein et al., U.S. Pat. No. 4,499,299, issued Feb. 12, 1985, and EPO Patent Application Publication Nos. 28,063; 110,541; 132,124; and 146,333, all of which are herein incorporated by reference.

More specifically, the Tetrazole Precursor of Scheme 2 above can be synthesized in the manner set forth in Scheme 5:

Scheme 5

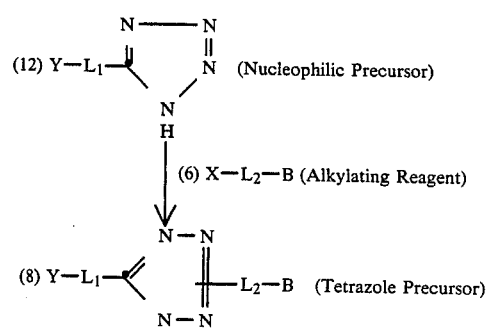

In the Scheme 5, X, $L_1$, $L_2$, and B are as described for Scheme 2. Y in the above Scheme is a hydroxy group or a protected hydroxy group.

The first reaction in Scheme 5 is an alkylation of the tetrazole, producing a mixture of N-1 and N-2 isomers of the Tetrazole Nucleophile. If Y in the Scheme is hydroxy, the reaction will also produce some alkyltetrazole dimers, trimers, tetramers, and so on. Thus, it is preferred to have Y as a protected hydroxy group. The alkylation is carried out under conditions described for Scheme 1. After the alkylation, the hydroxy protecting group is removed in a normal manner. The hydroxy group is converted to the halo compound by methods known in the art, such as by the use of the reagents $\phi_3PCl_2$, $\phi_3PBr_2$, $(\phi O)_3 \cdot P^{\oplus}CH_3I^-$, $PCl_5$, $PBr_3$, and the like.

Scheme 6 below sets forth below the synthesis for the Tetrazole Nucleophile of Scheme 3.

Scheme 6

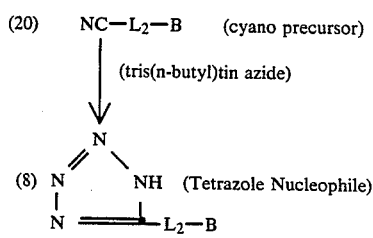

In Scheme 6, $L_2$ is as defined for Formula II and B is either a group of the formula $-COOR_8$ or is cyano. The above reaction employes the same conditions as the analogous reaction converting the cyano intermediates of Formula II to the tetrazole final products (A = 5-(tetrazolyl)) of Formula I. (When B above is also cyano, both nitriles are converted to tetrazole simultaneously).

The starting materials for Scheme 1 above when $L_1$ is phenyl are made by the Ullman reaction (see Weingarten, J. Org. Chem., 29 977) as depicted in Scheme 7.

Scheme 7

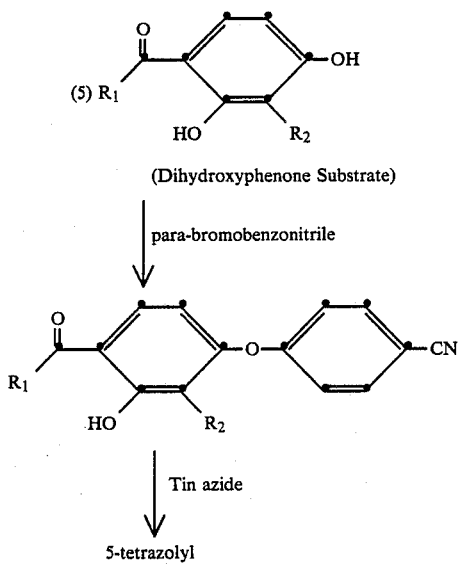

(5) (Dihydroxyphenone Substrate)

↓ para-bromobenzonitrile

↓ Tin azide 5-tetrazolyl

The reaction producing the phenoxybenzonitrile was carried out under standard Ullman conditions. Thus, equimolar amounts of the Dihydroxyphenone Substrate, p-bromo benzonitrile and potassium carbonate, and a slight molar excess of metallic copper powder, were added to pyridine and stirred at reflux temperatures for from 24 to 72 hours. The mixture was evaporated to dryness and the product is extracted into a polar organic solvent (for example, ethyl acetate), which is neutralized, washed, dried, filtered and concentrated. The phenoxybenzonitrile can be further purified by chromatography such as by HPLC over silica gel eluted with a gradient ethyl acetate in hexane.

The phenoxybenzonitrile is converted to the desired 5-tetrazolyl by methods described for converting the cyano intermediates to the tetrazolyl final products.

The compounds of Formula I should be useful in treating any condition, including clinical conditions, which is characterized by excessive release of leukotrienes $C_4$, $D_4$, or $E_4$ or any combination thereof. These conditions include immediate type hypersensitivity reactions such as asthma. Recent clinical studies have supported a role for a leukotriene antagonist in the treatment of asthma (Cloud et al., J. Allergy Clin. Immunol., 79 256 (1987)) thus providing further evidence of the intermediary of leukotrienes in clinical asthma. Further evidence obtained over the past few years has shown the presence of leukotrienes in sputum of patients with chronic bronchitis (Turnbull, et al., Lancet II, 526 (1977) and cystic fibrosis (Cromwell, et al., Lancet II, 164 (1981)), suggesting a role of leukotrienes in the pathology of those diseases as well. Furthermore, Lewis and colleagues [Int. J. Immunopharmacology, 4, 85 (1982)]have detected material in rheumatoid synovial fluid that reacts antigenically with antibody to $LTD_4$. This may hallmark the existence of leukotriene permeability factors that, together with $LTB_4$, augment the inflammatory process in the diseased joints. Therefore, the compounds described in this invention should also alleviate some of the symptoms of chronic bronchitis and cystic fibrosis and possibly rheumatoid arthritis by virtue of their ability to antagonize leukotrienes. The compounds are also useful for inhibiting the cardiovascular effects of leukotrienes thereby rendering them useful for treating conditions such as shock and ischemic heart disease. Evidence that leukotrienes are involved in cardiovascular conditions and in shock syndromes is provided by the work of Cook et al., J. Pharmacol. Exp. Ther., 235, 470–474 (1985); Eimerl et al., Am. J. Physiol., 251 H700–H709 (1986); Etemadi et al., Circ. Shock, 22, 55–63 (1987); and Hock and Lefer, Circ. Shock, 17, 263–272 (1985).

The term "excessive release" of leukotrienes refers to an amount of leukotrienes sufficient to cause the particular condition associated with such amount. The amount of leukotriene which is considered to be excessive will depend on a variety of factors, including the specific leukotriene(s) involved, the amount of leukotriene required to cause the particular condition, the tissue location, and the species of the mammal involved. As will be appreciated by those skilled in the art, the success of treating a mammal suffering from or susceptible to a condition characterized by an excessive release of leukotrienes with a compound of Formula I will be measured by the regression or prevention of the symptoms of the condition. The compounds of Formula I provide exceptionally high blood levels.

Leukotriene antagonism of the claimed final products was demonstrated by the following test procedure:

Male, Hartley guinea pigs weighing 200–450 grams were killed by decapitation. A section of terminal ileum was removed, the lumen cleaned, and the tissue divided into 2.5 cm segments. The ilea were mounted in 10 ml tissue baths containing Krebs-bicarbonate solution of the following composition in mmoles/liter: KCl, 4.6; $CaCl_2 \cdot 2H_2O$, 1.2; $KH_2PO_4$, 1.2; $MgSO_4 \cdot 7H_2O$, 1.2; NaCl, 118.2; $NaHCO_3$, 24.8; and dextrose, 10.0. The bath fluid was maintained at 37° C. and aerated with 95 percent oxygen and 5 percent $CO_2$. In addition, the buffer contained $1 \times 10^{-6}$M atropine to reduce ileal spontaneous activity. Isometric measurements were made with a Grass FT03C force-displacement transducer and recorded on a Grass polygraph as change in grams of force. A passive force of 0.5 g. was applied to the tissues. After an appropriate equilibration period, single submaximal control responses to pure $LTD_4$ were obtained. Following a five minute exposure of the ileum to an experimental drug, the control concentration of $LTD_4$ was added to the tissue bath. The response of the ileum to $LTD_4$ in the presence of the drug was compared to the response in the absence of the drug. Various degrees of $LTD_4$ antagonism were obtained using 2–4 different concentrations of an experimental compound on a single ileum. The antagonist concentration that produced 50% inhibition of the $LTD_4$ responses ($-\log IC_{50}$) was interpolated from these data using linear regression.

For some of the drugs in this series a more detailed analysis of $LTD_4$ antagonism was made. In these experiments, cumulative concentration-response curves were obtained to $LTD_4$ in guinea pig ileum and trachea. This was followed by a 30 minute incubation with various concentrations of the experimental drug. The concentration response curve to $LTD_4$ was then repeated in the presence of an antagonist. Only one concentration of antagonist was used on a single tissue. $K_B$ values were calculated by the method of Furchgott [Ann. N.Y. Acad. Sci., 139, 553 (1967)] using the following equation.

$$K_B = \frac{[\text{Antagonist}]}{\text{Dose Ratio} - 1}$$

Dose effect ratio refers to the concentration of agonist required to elicit 50 percent of the maximal response ($ED_{50}$) in the presence of the antagonist divided by the $ED_{50}$ in the absence of the antagonist. Calculations were performed with the aid of a computer and a digital plotter. The negative log of the dissociation $K_B$ ("$pK_B$") is given for some of the compounds in the table below.

The testing of the compounds in Formula I in these two procedures is summarized in Table I.

TABLE I

| Percent inhibition of $LTD_4$ evoked ileal contractions | | |
|---|---|---|
| Example No. | $-\log IC_{50}$ | $pK_B$ |
| 23A | 7.65 | — |
| 24 | 6.14 | — |
| 25 | 7.42 | — |
| 26 | 7.63 | — |
| 27 | 7.05 | — |
| 28 | 7.57 | — |
| 29 | 7.35 | — |
| 30 | 7.54 | — |
| 31 | 7.75 | 7.190 |
| 33 | 6.30 | — |
| 34 | 7.52 | — |
| 35 | 7.15 | — |
| 38 | 6.62 | — |
| 39 | 6.37 | — |
| 40 | 6.83 | — |
| 44 | 6.81 | — |
| 45 | 5.83 | — |
| 46 | 7.12 | — |
| 47 | 5.89 | — |
| 48 | 7.15 | — |
| 50 | 6.54 | — |
| 51 | 6.75 | — |
| 54 | — | 7.10 |
| 55 | — | 6.89 |
| 56 | — | 6.40 |
| 57 | — | 7.06 |
| 58 | — | 7.00 |
| 59 | 7.50 | — |
| 60 | 7.26 | — |
| 61 | 5.20 | — |
| 62 | 6.47 | — |
| 64 | 7.51 | — |
| 65 | 6.18 | — |
| 67 | 7.25 | — |
| 68 | 6.66 | — |
| *A | 6.68 | — |
| *B | 5.88 | — |
| *C | 5.82 | — |
| *D | 5.95 | — |
| *E | 6.83 | — |
| *F | 6.59 | — |
| *G | 6.3 | — |

*A 5-[4-(4-Acetyl-3-hydroxy-2-propylphenoxy)butyl]-2H—tetrazole-2-(acetic acid)
*B 5-[4-(4-Acetyl-3-hydroxy-2-propylphenoxy)butyl]-1H—tetrazole-1-(acetic acid)
*C 5-[3-(4-Acetyl-3-hydroxy-2-propylphenoxy)propyl]-2H—tetrazole-2-(acetic acid)
*D 5-[3-(4-Acetyl-3-hydroxy-2-propylphenoxy)propyl]-1H—tetrazole-1-(acetic acid)
*E 5-[6-(4-Acetyl-3-hydroxy-2-propylphenoxy)hexyl]-2H—tetrazole-2-(acetic acid)
*F 5-[6-(4-Acetyl-3-hydroxy-2-propylphenoxy)hexyl]-1H—tetrazole-1-(acetic acid)
*G 5-[5-(4-Acetyl-3-hydroxy-2-propylphenoxy)pentyl]-2H—tetrazole-2-(acetic acid)

A further measure of the final product's activity is their ability to decrease the pressor response in pithed rats that are challenged by $LTD_4$. This activity is measured by the following standard procedure Adult male Sprague-Dawley rats, weighting approximately 300–500 grams, are anesthetized with pentobarbital sodium (60 mg/kg, i.p.). The trachea is cannulated and the rats are ventilated with room air delivered from a rodent respirator (Harvard, model 680; tidal volume of 1 ml/100 grams body weight, 60 cycles/minute). Rats are pithed by passing a steel rod through the right orbit and down the entire length of the spinal column. The rod is left in position for the duration of the experiment. Pulsatile arterial blood pressure is measured from a cannulated carotid artery using a Stathamtransducer (P231D). Mean arterial blood pressure is calculated as diastolic pressure plus ⅓ pulse pressure. Drug solutions are administered i.v. through a catheter placed in a jugular vein. Arterial blood pressure is recorded on a multichannel oscillograph (Beckman, model R511A).

Groups of pithed rats, usually 4–6/group, are pretreated i.v. with a dose of test compound or vehicle (control experiments) 15 minutes prior to leukotriene $D_4$ challenge (10 μg/kg, i.v.). Usually 3–4 doses of the test compound are evaluated in a given study. Blood pressure responses to leukotriene $D_4$ in control and drug-treated pithed rats are then compared and an $ED_{50}$ dose of antagonist is estimated. $ED_{50}$ (95% confidence interval) is the calculated dose of antagonist (mg/kg, i.v.) required to decrease the pressor response to leukotriene $D_4$ by 50%.

The $ED_{50}$ values of selected final products of Formula I are set forth below in Table 2.

TABLE 2

| Pressor Response in Pithed Rats | |
|---|---|
| Example No. | $ED_{50}$ |
| A* | >30 |
| F* | 27.1 |
| B* | >30 |
| G* | >30 |
| E* | >30 |
| 51 | 18.3 |
| 45 | >30 |
| 47 | >30 |
| 50 | 17.3 |
| 44 | 10.6 |
| 46 | 8.1 |
| 48 | 9.9 |
| 29 | 8.7 |
| 27 | 12.7 |
| 25 | 8.4 |
| 23A | 7.5 |
| 28 | 9.7 |
| 26 | 18.6 |
| 39 | 25.8 |
| 30 | 16.8 |
| 54 | 22.4 |
| 34 | 25.5 |
| 31 | 6.5 |
| 57 | 19.8 |
| 55 | 22.0 |
| 35 | 27.5 |

*Letters correspond to Table 1

The compounds or formulations of the present invention may be administered by the oral and rectal routes, topically, parenterally, for example, by injection and by continuous or discontinuous intravenous infusion, in the form of, for example, tablets, lozenges, sublingual tablets, sachets, cachets, elixirs, suspensions, aerosols, ointments, for example, containing from 1 to 10% by weight of the active compound in a suitable base, soft and hard gelatin capsules, suppositories, injectable solutions and suspensions in physiologically acceptable media, and sterile packaged powders adsorbed onto a support material for making injectable solutions. Advantageously for this purpose, compositions may be provided in dosage unit form, preferably each dosage unit containing from about 5 to 500 mg (from about 5 to 50 mg in the case of parenteral or inhalation administration, and from about 25 to 500 mg in the case of oral or rectal administration) of a compound of Formula I. Therapeutically-effective, and thus leukotriene-antagonizing, dosages of from about 0.5 to 300 mg/kg per day, preferably 0.5 to 20 mg/kg, of the compound of Formula I be administered although it will, of course, readily be understood that the amount of the compound or compounds of Formula I actually to be administered will be determined by a physician, in the light of all the relevant circumstances including the condition to be treated, the choice of compound to be administered and the choice of route of administration and therefore the above preferred dosage range is not intended to limit the scope of the present invention in any way.

The pharmaceutical formulations of the present invention normally will consist of at least one compound of Formula I mixed with a carrier, or diluted by a carrier, or enclosed or encapsulated by an ingestible carrier in the form of a tablet, capsule, sachet, cachet, paper or other container or by a disposable container such as an ampoule. A carrier (or diluent) may be a solid, semisolid or liquid material which serves as a vehicle, excipient or medium for the active therapeutic substance.

Some examples of the pharmaceutically-acceptable carriers which may be employed in the pharmaceutical formulation of the present invention are lactose, dextrose, sucrose, sorbitol, mannitol, propylene glycol, liquid paraffin, white soft paraffin, kaolin, fumed silicon dioxide, microcrystalline cellulose, calcium silicate, silica, polyvinylpyrrolidone, cetostearyl alcohol, starch, modified starches, gum acacia, calcium phosphate, cocoa butter, ethoxylated esters, oil of theobroma, arachis oil, alginates, tragacanth, gelatin, syrup, methyl cellulose, polyoxyethylene sorbitan monolaurate, ethyl lactate, methyl and propyl hydroxybenzoate, sorbitan trioleate, sorbitan sesquioleate and oleyl alcohol and propellants such as trichloromonofluoromethane, dichlorodifluoromethane and dichlorotetrafluoroethane. In the case of tablets, a lubricant may be incorporated to prevent sticking and binding of the powdered ingredients in the dies and on the punch of the tableting machine. For such purpose there may be employed for instance aluminum, magnesium or calcium stearates, talc or mineral oil.

Preferred pharmaceutical formulations of the present invention are capsules, tablets, suppositories, injectable solutions, creams and ointments. Especially preferred are formulations for inhalation application, such as an aerosol, for oral ingestion and solutions for intravenous injection.

A preferred pharmaceutical formulation of the instant invention comprises a therapeutically-effective amount of the preferred compounds of Formula I and a pharmaceutically-acceptable carrier, with the most preferred formulations comprising a therapeutically-effective amount of the compound of Example 23A (or a pharmaceutically-acceptable base-addition salt thereof) or the sodium salt of the compound of Example 23A and a pharmaceutically-acceptable carrier.

Preferred methods of treating a mammal suffering from or susceptible to any condition characterized by an excessive release of leukotrienes $C_4$, $D_4$, or $E_4$, or any combination thereof, which comprises administering to said mammal a leukotriene antagonizing amount of the compound of Example 23A (or a pharmaceutically-acceptable salt thereof), the sodium salt of the compound of Example 23A, or a compound of the preferred compounds of claim 1.

The following Examples and Preparations are provided merely to further illustrate the invention. The scope of the inventon is not to be construed as merely consisting of the following Examples.

In the following Examples and Preparations, melting point, nuclear magnetic resonance spectra, high pressure liquid chromatography, ethyl acetate, N,N-dimethylformamide, methyl ethyl ketone, 1,2-dimethoxyethane and hexamethylphosphoramide are abbreviated m.p., n.m.r., HPLC, EA, DMF, MEK, DME, and HMPA, respectively. (The reported melting points are uncorrected).

Nuclear Magnetic Resonance spectra were obtained on a General Electric Model QE-300 300 MHz instrument. HPLC were obtained on a Waters Associates Prep 500 ® Preparatory Scale HPLC equipped with PREPPAK ® 500 silica columns.

Experimental Section

EXAMPLE 1

5-[4-(4-Acetyl-3-hydroxy-2-(n-propyl)phenoxy)butyl]-2-(5-valeronitrile)-2H-tetrazole and the corresponding 1H-1-tetrazole isomer.

Under a nitrogen atmosphere, 5-4-(4-acetyl-3-hydroxy-2-(n-propyl)phenoxy)butyl]-2H-tetrazole (15.92 g, 50.00 mmol), potassium carbonate (6.95 g, 50.3 mmol), potassium iodide (8.65 g, 52.1 mmol), MEK (500 ml), and 5-bromovaleronitrile (7.0 ml, 57 mmol) were combined. The resultant reaction mixture was stirred at reflux temperature for 6 hours. The reaction mixture was allowed to cool to room temperature and stirred at room temperature for 48 hours. The reaction mixture was filtered and the filtrate was concentrated under reduced pressure. The resultant residue was partitioned between ethyl acetate (500 ml) and water 200 ml). The layers were separated and the organic phase washed with brine (100 ml), dried over magnesium sulfate, and concentrated under reduced pressure. The resultant residue was flash chromatographed (Kieselgel ® 60, 230–400 mesh, column: 7.5 cm diameter, 15 cm length) eluted with a step gradient of 1:1 ethyl acetate:hexane to 4:1 ethyl acetate:hexane to yield 13.6 g of the higher $R_f$ regioisomer (5-[4-(4-acetyl-3-hydroxy-2-(n-propyl)phenoxy)butyl]-2-(5-valero-nitrile)-2H-tetrazole) and 5.50 g of the lower $R_f$ (1H-1-tetrazole isomer. Both isomers were confirmed by n.m.r. and then were used without further purification. 2-H (higher $R_f$)isomer of the title product: n.m.r. (300 MHz, CDCl$_3$) δ: 12.74 (s, 1H); 7.59 (d, 1H); 6.43 (d, 1H); 4.64 (t, 2H); 4.08 (t, 2H); 3.00 (t, 2H); 2.64 (t, 2H); 2.58 (s, 3H); 2.42 (t, 2H); 2.18 (m, 2H); 2.04 (m, 2H); 1.94 (m, 2H); 1.70 (m, 2H); 1.54 (m, 2H); 0.94 (t, 3H).

m.p. 33–35° C.;

Analysis calculated for $C_{21}H_{29}N_5O_3$:
Theory: C, 63.14; H, 7.32; N, 17.53;
Found: C, 63.23; H, 7.44; N, 17.64

1-H (lower $R_f$) isomer of the title product:
m.p. 57–59° C.

Analysis calculated for $C_{21}H_{29}N_5O_3$:
Theory: C, 63.14; H, 7.32; N, 17.53;
Found: C, 63.01; H, 7.17; N, 17.66;

n.m.r. (300 MHz, CDCl$_3$) δ: 12.75 (s, 1H); 7.59 (d, 1H); 6.42 (d, 1H); 4.33 (t, 2H); 4.10 (t, 2H); 2.94 (t, 2H); 2.62 (t, 2H); 2.57 (s, 1H); 2.44 (t, 2H); 2.10 (m, 4H); 2.00 (m, 2H); 1.74 (m, 2H); 1.52 (m, 2H); 0.92 (t, 3H).

EXAMPLE 2

5-[4-(4-Acetyl-3-hydroxy-2-(n-propyl)phenoxy)butyl]-2-(4-butyronitrile)-2H-tetrazole and the corresponding 1H-1-tetrazole isomer Under a nitrogen atmosphere, potassium carbonate (4.19 g, 30.3 mmol), potassium iodide (5.05 g, 30.4 mmol), 5-[4-(4-acetyl-3-hydroxy-2-(n-propyl)phenoxy)-butyl]2H-tetrazole (9.56 g, 30.0 mmol), MEK (300 ml), and 4bromobutyronitrile (3.5 ml, 34 mmol) were combined and the resultant reaction mixture was stirred at reflux temperature for 28 hours. The reaction mixture was stirred at room temperature for an additional 24 hours, filtered, and the filtrate was concentrated under reduced pressure. The resultant oil was taken up in ethyl acetate (250 ml) and 5% sodium bicarbonate (100 ml). The phases were separated and the organic phase was washed with brine (50 ml), dried over magnesium sulfate, filtered, then concentrated in vacuo. The concentrate was chromatographed on preparatory-scale HPLC (PREPPAK® 500 silica columns) eluted with a gradient of 1:1 ethyl acetate:hexane (4L) to 3:1 ethyl acetate: hexane (4L). The higher $R_f$ regioisomer-containing fractions were combined and concentrated to give 7.70 g (67%) of that isomer as a yellow oil and the fractions containing the lower $R_f$ regioisomer were combined and concentrated to give 2.70 g (23%) of that isomer as a yellow oil. The higher $R_f$ regioisomer was flash chromatographed (Kieselgel® 60, 230–400 mesh, eluted with a 1:1 ethyl acetate:hexane) mixture to yield 9.5 g (65%) of 5-[4-(4-acetyl-3-hydroxy-2-(n-propyl)-phenoxy)butyl]-2-(4-butyronitrile)-2H-tetrazole: n.m.r. (300 MHz, CDCl$_3$) δ: 12.74 (s, 1H); 7.58 (d, 1H); 6.43 (d, 1H); 4.73 (t, 2H); 4.08 (t, 2H); 3.00 (t, 2H); 2.64 (t, 2H); 2.59 (s, 3H); 2.50 (t, 2H); 2.37 (m, 2H); 2.04 (m, 2H); 2.01 (m, 2H); 1.54 (m, 2H); 0.94 (t, 3H).

The lower $R_f$ isomer was allowed to stand for several days then was recrystallized from ether to give 0.97 g of the corresponding 1H-1-tetrazole isomer: m.p. 62–63° C. n.m.r. (300 MHz, CDCl$_3$) δ: (critical peak only): 4.41 (t, 2H).

Analysis calculated for $C_{20}H_{27}N_5O_3$:
Theory: C, 62.32; H, 7.06; N, 18.17;
Found: C, 62.48; H, 6.91; N, 18.38.

EXAMPLE 3

5-[4-(4-Acetyl-3-hydroxy-2-(n-propyl)phenoxy)butyl]-2-(6-cyanohexyl)-2H-tetrazole The procedure of Example 2 was repeated using the following reagents and amounts:
potassium carbonate (4.23 g, 30.6 mmol)
potassium iodide (4.98 g, 29.5 mmol)
1-bromo-6-cyanohexane (5.4 ml, 33.4 mmol)
MEK (300 ml)
5-[4-(4-Acetyl-3-hydroxy-2-(n-propyl)phenoxy)-butyl]-2H-tetrazole (9.55 g, 30.0 mmol)
These reactants were combined and heated to reflux temperature refluxed for 72 hours, cooled, filtered, and concentrated in vacuo. The regioisomers were separated by preparatory-scale HPLC (silica column) eluted with a solvent gradient of 40% ethyl acetate:hexane (4L) to 7:3 ethyl acetate:hexane (4L) followed by 7:3 ethyl acetate: hexane (1L). Product-containing fractions were combined and concentrated under reduced pressure to yield 10.0 g (78%) of 5-[4-(4-Acetyl-3-hydroxy-2-(n-propyl)phenoxy) butyl]-2H-2-(6-cyanohexyl)-tetrazole which was used without further purification. n.m.r. (300 MHz, CDCl$_3$) δ: 7.58 (d, 1H); 6.42 (d, 1H); 4.57 (t, 2H); 4.07 (t, 2H); 2.98 (t, 2H); 2.62 (t, 2H); 2.56 (s, 3H); 2.34 (t, 2H); 2.02 (m, 4H); 1.93 (m, 2H); 1.66 (m, 2H); 1.52 (m, 4H); 1.37 (s, 2H); 0.92 (t, 3H).

EXAMPLE 4

5-[4-(4-Acetyl-3-hydroxy-2-(n-propyl)phenoxy)butyl]-2-(6-hexanonitrile)-2H-tetrazole and the corresponding 1H-1-tetrazole isomer This procedure follows the procedure of Example 1 in general, using the following amounts and reagents:
potassium carbonate (4.15 g, 30.0 mmol);
potassium iodide (4.98 g, 29.5 mmol);
6-bromohexanonitrile (5.90 g, 33.2 mmol);
MEK (300 ml); and
5-[4-(4-acetyl-3-hydroxy-2-(n-propyl)phenoxy)butyl]-2H-tetrazole (9.55 g, 30.0 mmol).
The reaction mixture containing the above reactants was heated to reflux for 3 hours, then cooled and filtered. After the usual work-up the yellow oil was chromatographed on the preparatory-scale HPLC (silica column) eluted with a solvent gradient of 1:1 ethyl acetate:hexane (4L) to 3:1 ethyl acetate:hexane (4L) followed by a wash of 3:1 ethyl acetate:hexane (1L). The product-containing fractions were combined and concentrated in vacuo to yield 10.0 g (81%) of the higher $R_f$ regioisomer: 5-[4-(4-acetyl3-hydroxy-2-(n-propyl)phenoxy)butyl]-2-(6-hexanonitrile)-2H-tetrazole: n.m.r. (300 MHz, CDCl$_3$) δ: 12.75 (s, 1H); 7.59 (d, 1H); 6.43 (d, 1H); 4.60 (t, 2H); 4.09 (t, 2H); 3.00 (t, 2H); 2.64 (t, 2H); 2.58 (s, 3H); 2.37 (t, 2H); 2.06 (m, 4H); 1.94 (m, 2H); 1.73 (m, 2H); 1.55 (m, 4H); 0.94 (t, 3H).

EXAMPLE 5

5-[4-(4-Acetyl-3-hydroxy-2-(n-propyl)phenoxy)butyl]-2-(p-methylbenzonitrile)-2H-tetrazole and the corresponding 1H-1-tetrazole isomer.

In the procedure that follows generally that of Example 1, the following amounts of reagents were used:
potassium carbonate (13.89 g, 100.5 mmol);
potassium iodide (16.62 g, 100.1 mmol);
α-bromo-p-tolunitrile (20.0 g, 101 mmol);
MEK (900 ml); and
5-[4-(4-acetyl-3-hydroxy-2-(n-propyl)phenoxy)butyl]-2H-tetrazole (31.84 g, 100.0 mmol).
This reaction mixture was heated to reflux temperature for 2 hours then allowed to stand at room temperature for 48 hours. After the usual concentration, washing and drying procedures, 47 g of reddish brown oil was obtained. The isomers were separated along the lines of Example 2 with a preparatory-scale HPLC using 20 to 50% ethyl acetate in hexane as the eluant. The product-containing fractions were combined and concentrated in vacuo. The higher $R_f$ fraction was recrystallized from an ether and hexane mixture to give 22.2 g, 51% of the product 5-[4-(4-acetyl-3-hydroxy-2-(n-propyl)phenoxy)butyl]-2-(p-methylbenzonitrile)-2H-tetrazole: m.p. 73°–75° C;
Analysis calculated for $C_{24}H_{27}N_5O_3$:
Theory: C, 66.50; H, 6.28; N, 16.16;
Found: C, 66.46; H, 6.43; N, 15.99.

EXAMPLE 6

5-[4-(4-Acetyl-3-hydroxy-2-(n-propyl)phenoxy)-butyl]-2-(m-methylbenzonitrile)-2H-tetrazole and the corresponding 1H-1-tetrazole isomer In a procedure that was similar to that of Example 1, the following amounts of reagents were used:
potassium carbonate(7.0 g, 51 mmol);
potassium iodide (9.4 g, 57 mmol);
α-bromo-m-tolunitrile (11.4 g, 55.2 mmol);
MEK (500 ml); and
5-[4-(4-acetyl-3-hydroxy-2-(n-propyl)phenoxy)-butyl]-2H-tetrazole (15.92 g, 50.0 mmol)

The above reaction mixture was stirred and heated to reflux temperature for 3 hours and then stirred at room temperature overnight. After the usual concentration, washing, and drying steps, the concentrate gave a reddish brown oil that was separated on a preparatory-scale HPLC (silica column) eluted with a gradient of 20% ethyl acetate:hexane and 1% acetic acid (4L) to 40% ethyl acetate:hexane and 1% acetic acid (4L) followed by a wash of 40% ethyl acetate: hexane plus 1% acetic acid, then eluted with another gradient of 40% ethyl acetate:hexane plus 1% acetic acid (2L) to 60% ethyl acetate:hexane plus 1% acetic acid (2L). The fractions containing the higher $R_f$ regioisomer were combined and concentrated to give 12 g of a reddish brown oil. Some crystals formed upon standing. An attempt at crystallization from ether/hexane mixture left an oil which was permitted to stand with the previously-collected seed crystals overnight. This crystallization yielded 8.98 g, 41%, of 5-[4-(4-acetyl-3-hydroxy-2-(n-propyl)phenoxy)butyl]-2-(m-methylbenzonitrile)-2H-tetrazole which was used without further purification; m.p. 48–50° C.;

Analysis calculated for $C_{24}H_{27}N_5O_3$:
  Theory: C, 66.50; H, 6.28; N, 16.16;
  Found: C, 66.72; H, 6.44; N, 16.23;

The fractions corresponding to the lower $R_f$ regioisomer (the 1H-1-tetrazole isomer) were combined and concentrated. Factions were combined and permitted to stand overnight which gave crystals that were collected and rinsed with ether then dried for approximately 2 hours at room temperature in vacuo to give 3.57 g, 16% of the corresponding 1H-1-tetrazole isomer; m.p. 102–105° C.

Analysis calculated for $C_{24}H_{27}N_5O_3$:
  Theory: C, 66.50; H, 6.28; N, 16.16;
  Found: C, 66.42; H, 6.46; N, 16.33.

The filtrate from these crystals were combined with any remaining chromatography fractions of the same isomer, concentrated, and dried in vacuo overnight to give an additional 3.9 g of crude product. The crude product was recrystallized from a mixture of ethyl acetate/hexane to yield 3.45 g, 16%, of the 1H-1-tetrazole isomer.

EXAMPLE 7

5-[5-(4-Acetyl-3-hydroxy-2-(n-propyl)phenoxy)pentyl]-2-(4-butyronitrile)-2H-tetrazole and the corresponding 1H-1-tetrazole isomer In a procedure that was similar to that of Example 1, the following reagents and amounts thereof were combined:
potassium carbonate (1.26 g, 9.12 mmol);
potassium iodide (1.54 g, 9.28 mmol);
MEK (150 ml);
4-bromobutyronitrile (1.1 ml, 10.7 mmol); and
5-5-(4-acetyl-3-hydroxy-2-(n-propyl)phenoxy)pentyl]-2H-tetrazole (3.02 g, 9.09 mmol).

The reaction mixture was stirred and heated at reflux temperature for 4 hours and then at room temperature for 24 hours. The reaction mixture was filtered, concentrated under reduced pressure, and partitioned in the usual manner. The ethyl acetate solution of the partition was concentrated under reduced pressure and the resultant oil (4.17 g) was flash chromatographed (Kieselgel 60, 230–400 mesh, column: 7.5 cm (dia), 15 cm (length)) eluted with a gradient of 50% ethyl acetate in hexane (2 l) 60% ethyl acetate in hexane (2 l) and 65% ethyl acetate in hexane (2 l). After combining the product-containing fractions and concentrating, 5-[5-(4-acetyl-3-hydroxy-2-(n-propyl)phenoxy)pentyl]-2-(4-butyronitrile)-2H-tetrazole was recovered as a yellow oil (2.66 g, 72% yield) and the corresponding 1H-1-tetrazole isomer was recovered as a crystalline white solid (0.77 g, 21%) with an m.p. of 104°–105° C. 2H-tetrazole isomer of the title product:

Analysis calculated for $C_{21}H_{29}N_5O_3$: Theory: C, 63.14; H, 7.32; N, 17.53; Found: C, 62.90; H, 7.03; N, 17.33.

EXAMPLE 8

5-[5-(4-Acetyl-3-hydroxy-2-(n-propyl)phenoxy)pentyl]-2-(S-valeronitrile)-2H-tetrazole and the corresponding 1H-1-tetrazole isomer In a procedure that was similar to that of Example 1, the following reagents and amounts were combined:
potassium carbonate (1.41 g, 10.2 mmol);
potassium iodide (1.71 g, 10.3 mmol);
5-bromovaleronitrile (1.4 ml, 11.4 mmol);
MEK (100 ml); and
5-[5-(4-acetyl-3-hydroxy-2-(n-propyl)phenoxy)pentyl]-2H-tetrazole (3.32 g, 9.99 mmol).

The above reaction mixture was stirred and heated to reflux temperature overnight then cooled and filtered. The filtrate was concentrated under reduced pressure and was permitted to stand at room temperature overnight. The concentrate was partitioned and the organic phase was washed and dried and concentrated in the usual manner. The concentrate was then flash chromatographed over a column similar to Example 7 that was eluted with 40% ethyl acetate/60% hexane. The chromatography yielded 5-[4-(4-acetyl-3-hydroxy-2-(n-propyl)phenoxy)pentyl]-2H-2-(5-valeronitrile)-tetrazole (2.76 g, 67% yield) and the corresponding 1H-1-tetrazole isomer (0.89 g, 22%). 2H-2-tetrazole isomer of the title product: n.m.r. (300 MHz, CDCl$_3$) δ: 12.74 (s, 1H); 7.58 (d, 1H); 6.42 (d, 1H); 4.63 (t, 2H); 4.04 (t, 2H); 2.93 (t, 2H); 2.61 (t, 2H); 2.56 (s, 3H); 2.41 (t, 2H); 2.17 (m, 2H); 1.88 (m, 4H); 1.68 (m, 2H); 1.53 (m, 2H); 0.92 (t, 3H).

EXAMPLE 9

5-[6-(4-Acetyl-3-hydroxy-2-(n-propyl)phenoxy)hexyl]-2-(4-butyronitrile)-2H-tetrazole and the corresponding 1H-1-tetrazole isomer In a procedure similar to that of Example 1, the following reagents and amounts were combined:
potassium carbonate (1.40 g, 10.1 mmol);
potassium iodide (1.68 g, 10.1 mmol);
MEK (150 ml);
4-bromobutyronitrile (1.2 ml, 11.7 mmol); and
5-[6-(4-acetyl-3-hydroxy-2-(n-propyl)phenoxy)hexyl]-2H-tetrazole (3.49 g, 10.1 mmol).

This mixture was stirred and heated to reflux temperature for 3.5 hours then stirred overnight at room temperature. After the usual isolation of the crude product, flash chromatography of the concentrated ethyl acetate layer yielded 2.92 g, 70% of 5-[6-(4-acetyl-3-hydroxy-2-(n-propyl)phenoxy)hexyl]-2H-2-(4-butyronitrile-tetrazole and 1.04 g, 25% of the corresponding 1H-1-tetrazole isomer. 1H isomer: n.m.r. (300 MHz, CDCl$_3$) δ: 12.74 (s, 1H); 7.57 (d, 1H); 6.41 (d, 1H); 4.39 (t, 2H); 4.02 (t, H); 2.88 (t, 2H); 2.61 (t, 2H); 2.55 (s, 3H); 2.50 (t, 3H). H); 2.35 (m, 2H); 1.85 (m, 4H); 1.53 (m, 6H); 0.92 (t,

EXAMPLE 10

5-[6-(4-Acetyl-3-hydroxy-2-(n-propyl)phenoxy)hexyl]-2-(5-valeronitrile)-2H-tetrazole and the corresponding 1H-1-tetrazole isomer In a manner similar to that of Example 1, the following reagents and amounds were combined:
potassium carbonate (1.40 g, 10.4 mmol);
potassium iodide (1.75 g, 10.5 mmol);
MEK (100 ml);
5-bromovaleronitrile (1.30 ml, 10.6 mmol); and
5-6-(4-acetyl-3-hydroxy-2-(n-propyl)phenoxy)hexyl]-2H-tetrazole (3.47 g, 10.0 mmol).

The above reaction mixture was heated to reflux for 2.5 hours and then stirred at room temperature for eight days. The reaction mixture was filtered and concentrated in vacuo. The resultant residue was flash chromatographed as in Example 8, eluting the column with a 2:3 mixture of ethyl acetate:hexane (2L) followed sequentially by a mixture of 1:1 ethyl acetate:hexane (2 l) then a mixture of 3:2 ethyl acetate:hexane (3 l). Combining and concentrating the product-containing fractions gave 3.02 g, 70% yield, of 5-[6-(4-acetyl-3-hydroxy-2-(n-propyl)phenoxy)hexyl]-2-(5-valeronitrile)-2H-tetrazole and 0.98 g, 23% yield of the corresponding 1H-1-tetrazole isomer. 2H-2-Tetrazole isomer of the title product: n.m.r. (300 MHz, CDCl$_3$) δ: 12.74 (s, 1H); 7.58 (d, 1H); 6.42 (d, 1H); 4.62 (t, 2H); 4.02 (t, 2H); 2.90 (t, 2H); 2.62 (t, 2H); 2.56 (s, 3H); 2.41 (t, 2H); 2.17 (m, 2H); 1.83 (m, 4H); 1.69 (m, 2H); 1.51 (m, 6H); 0.93 (t, 3H).

Analysis calculated for C$_{23}$H$_{33}$N$_5$O$_3$: Theory: C, 64.61; H, 7.78; N, 16.38; Found: C, 64.35; H, 7.68; N, 16.31.

1H-1-tetrazole isomer of the title product:
Analysis calculated for C$_{23}$H$_{33}$N$_5$O$_3$: Theory: C, 64.61; H, 7.78; N, 16.38; Found: C, 64.40; H, 7.73; N, 16.24.

n.m.r. (300 MHz, CDCl$_3$) δ: (distinguishing peak only): 4.32, (t, 2H).

EXAMPLE 11

Ethyl 5-[4-(4-acetyl-3-hydroxy-2-propylphenoxy]butyl]-2H-tetrazole-2-(3-propionate) and the corresponding 1H-1-tetrazole isomer Under a nitrogen atmosphere, potassium carbonate (4.17 g, 30.2 mmol), potassium iodide (4.99 g, 30.1 mmol), and MEK (300 ml) were combined and stirred. To the stirring mixture was added 5-[4-(4-acetyl-3-hydroxy-2-(n-propyl)phenoxy)butyl]-2H-tetrazole (9.55 g, 30.0 mmol) and ethyl-3-bromopropionate (3.90 ml, 30.4 mmol) and the mixture was stirred and heated to reflux temperature for 1.75 hours then stirred at room temperature for 24 hours. The mixture was then stirred and heated to reflux temperature for 4 hours, and additional MEK (100 ml) and ethyl-3-bromopropronate (1.0 ml) were added. The mixture was stirred 2 hours at reflux then stirred overnight at room temperature. The mixture was filtered, concentrated in vacuo and the residue was first partitioned between a mixture of ethyl acetate (350 ml) and ether (250 ml) and 5% sodium bicarbonate solution (100 ml). The phases were separated and the organic phase was washed with brine, dried over magnesium sulfate and concentrated under reduced pressure to give 9.5 g of an oil. The oil was subjected to chromatography on a preparatory-scale HPLC (silica column) eluted with a solvent gradient of 20% ethyl acetate in hexane (4 l) to 40% ethyl acetate in hexane (4 l) followed by an additional amount of 40% ethyl acetate in hexane (4 l), 1:1 ethyl acetate:hexane (2 l), and finally ethyl acetate (1 l). The fractions containing the higher R$_f$ isomer were combined and concentrated in vacuo to an oil. The fractions containing the lower R$_f$ compound were stored at room temperature over the weekend. The higher R$_f$ isomer was twice taken up in carbon tetrachloride and concentrated in vacuo. The resultant residue was taken up in a mixture of hexane and ether and reconcentrated to leave 2.08 of ethyl 5-4-(4-acetyl-3-hydroxy-2-propylphenoxy]butyl]-2H-tetrazole-2-propionate.

The residue containing the lower R$_f$ isomer was triturated with 3 portions (75 ml) each of hot diethylether. The ether washes were combined and concentrated under reduced pressure to leave an oil and solid. The oil and solid were flash chromatographed (Kieselgel® 60, 230–400 mesh) eluted with a 3:2 mixture of hexane:ethyl acetate as eluant to recover 1.2 g of the corresponding 1H-1-tetrazole isomer. 2H-2-tetrazole isomer of the title product: n.m.r. (300 MHz, CDCl$_3$) δ: 12.73 (s, 1H); 7.58 (d, 1H); 6.42 (d, 1H); 4.85 (t, 2H); 4.16 (q, 2H); 4.06 (t, 2H); 3.05 (t, 2H); 2.97 (t, 2H); 2.62 (t, 2H); 2.56 (s, 3H); 1.99 (m, 2H); 1.92 (m, 2H); 1.52 (m, 2H); 1.25 (t, 3H); 0.92 (t, 3H).

Analysis calculated for C$_{21}$H$_{30}$N$_4$O$_5$: Theory: C, 60.27; H, 7.23; N, 13.39; Found: C, 60.51; H, 7.14; N, 12.98.

1H-1-tetrazole isomer of the title product: n.m.r. (300 MHz, CDCl$_3$) δ: 12.74 (s, 1H); 7.57 (d, 1H); 6.41 (d, 1H); 4.49 (t, 2H); 4.11 (m, 4H); 3.05 (m, 4H); 2.62 (t, 2H); 2.57 (s, 3H); 2.08 (m, 2H); 2.00 (m, 2H); 1.52 (m, 2H); 1.23 (t, 3H); 0.92 (t, 3H).

EXAMPLE 12

Ethyl 5-4-(4-acetyl-3-hydroxy-2-propylphenoxy]butyl]-2H-tetrazole-2-(4-butanonate) and the corresponding 1H-1-tetrazole isomer Under a nitrogen atmosphere, potassium carbonate (4.15 g, 30.0 mmol), potassium iodide (4.98 g, 30.0 mmol), MEK (300 ml), and the 5-[4-(4-acetyl-3-hydroxy-2-(n-propyl)phenoxy)butyl]-2H-tetrazole (9.55 g, 30.0 mmol) were combined and stirred. To the stirring mixture was added ethyl-4-bromobutanoate (5.00 ml, 33.2 mmol). The resultant mixture was heated at reflux temperature for 1.5 hours then stirred at room temperature overnight.

The reaction mixture was filtered through a thin pad of Celite ™ and the filtrate was concentrated under reduced pressure. The resultant residue was partitioned between ethyl acetate (250 ml) and 5% sodium bicarbonate solution (100 ml). The phases were separated and the organic phase was washed with brine (50 ml), dried over magnesium sulfate, and concentrated in vacuo to give 15 g of a crude product. The crude product was chromatographed by preparatory-scale HPLC (on a silica column) eluted with a gradient of 20% ethyl acetate in hexane (4 l) to 50% ethyl acetate in hexane (4 l) followed by mixtures of 1:1 ethyl:acetate hexane (4 l), 3:2 ethyl acetate:hexane (2 l) and finally 7:3 ethyl acetate:hexane (1 l). The fractions containing the higher $R_f$ isomer were combined and concentrated to yield 9.34 g, 72% of ethyl 5-[4-(4-acetyl-3-hydroxy-2-propylphenoxy)butyl]-2H-tetrazole-2-(4-butanoate).

The fractions containing the lower $R_f$ regioisomer were combined and concentrated to give 3.50 g, 27% of the corresponding 1H-1-tetrazole isomer. 2H-2-tetrazole isomer of the title product: n.m.r. (300 MHz, CDCl$_3$) δ: 12.73 (s, 1H); 7.58 (d, 1H); 6.42 (d, 1H); 4.65 (t, 2H); 4.14 (q, 2H); 4.07 (t, 2H); 2.98 (t, 2H); 2.62 (t, 2H); 2.56 (s, 3H); 2.34 (m, 4H); 2.00 (m, 2H); 1.93 (m, 2H); 1.52 (m, 2H); 1.25 (t, 3H); 0.92 (t, 3H).

EXAMPLE 13

Ethyl 5-[4-(4-acetyl-3-hydroxy-2-propylphenoxy]butyl]-2H-tetrazole-2-(5-pentanoate) and the corresponding 1H-1-tetrazole isomer In a procedure similar to that of Example 12, the following reagents and amounts were combined and stirred:
potassium carbonate (4.15 g, 30.0 mmol);
potassium iodide (5.00 g, 30.1 mmol);
MEK (300 ml);
ethyl 5-bromopentanoate (5.5 ml, 34 mmol); and
5-[4-(4-acetyl-3-hydroxy-2-(n-propyl)phenoxy)butyl]-2H-tetrazole (9.55 g, 30.0 mmol).

The above reagents were stirred and heated to reflux temperature for 5 hours, allowed to cool, then filtered and concentrated in vacuo. The concentrate was partitioned, dried and filtered as in Example 12 then purified by Preparatory-scale HPLC (silica column) eluted with a gradient of 1:3 ethyl acetate:hexane (4 l) to 1:1 ethyl acetate:hexane (4 l) followed by a gradient of 1:1 ethyl acetate:hexane (2 l) to 3:1 ethyl acetate:hexane (2 l). The product-containing fractions for the higher $R_f$ isomer were combined and concentrated to give 8.95 g, 67% yield of ethyl 5-[4-(4-acetyl-3-hydroxy-2-propylphenoxy]butyl]-2H-tetrazole-2-(5-pentanoate). Similarly, the lower $R_f$ isomer-containing fractions were combined and concentrated to yield 3.7 g, 28% of the corresponding 1H-1-tetrazole isomer. 2H-2-Tetrazole isomer of the title product: n.m.r. (300 MHz, CDCl$_3$) δ: 12.74 (s, 1H); 7.58 (d, 1H); 6.42 (d, 1H); 4.58 (t, 2H); 4.12 (q, 2H); 4.07 (t, 2H); 2.98 (t, 2H); 2.63 (t, 2H); 2.56 (s, 3H); 2.35 (t, 2H); 2.02 (m, 4H); 1.93 (m, 2H); 1.66 (m, 2H); 1.52 (m, 2H); 1.25 (t, 3H); 0.92 (t, 3H).

1H-1-Tetrazole isomer of the title product:
Analysis calculated for C$_{23}$H$_{34}$N$_4$O$_5$: Theory: C, 61.86; H, 7.67; N, 12.55; Found: C, 62.0%; H, 7.40; N, 12.33.

EXAMPLE 14

Ethyl 5-[4-(4-acetyl-3-hydroxy-2-propylphenoxy]butyl]-2H-tetrazole-2-(6-hexanoate) and the corresponding 1H-1-tetrazole isomer In a procedure similar to Example 12, the following reagents and amounts were used:
potassium carbonate (4.15 g, 30.0 mmol);
potassium iodide (5.08 g, 30.6 mmol);
MEK (300 ml); 5-[4-(4-acetyl-3-hydroxy-2-(n-propyl)-phenoxy)butyl]-2H-tetrazole (9.55 g, 30.0 mmol); and
ethyl 6-bromohexanoate (7.70 g, 32.8 mmol).

The above reactants were combined, stirred and heated to reflux for 3 hours. The reaction mixture was allowed to stir at room temperature overnight and worked up in the usual manner. The resultant residue was chromatographed using a preparatory-scale HPLC (silica column) eluted with a gradient of a 1:3 ethyl acetate:hexane mixture to a 1:1 ethyl acetate:hexane mixture to yield approximately 7.9 g, 57% of ethyl 5-[4-(4-acetyl-3-hydroxy-2-propylphenoxy]butyl]-2H-tetrazole-2-(6-hexanoate): 2H-2-Tetrazole isomer of the title product: m.p. 34.5°–36° C; n.m.r. (300 MHz, CDCl$_3$) δ: 12.73 (s, 1H); 7.58 (d, 1H); 6.42 (d, 1H); 4.55 (t, 2H); 4.11 (q, 2H); 4.06 (t, 2H); 2.97 (t, 2H); 2.62 (t, 2H); 2.56 (s, 3H); 2.29 (t, 2H); 2.01 (m, 4H); 1.92 (m, 2H); 1.67 (m, 2H); 1.52 (m, 2H); 1.37 (m, 3H); 1.24 (t, 3H); 0.92 (t, 3H).

Analysis Calculated for C$_{24}$H$_{36}$N$_4$O$_5$: Theory: C, 62.59; H, 7.88; N, 12.16; Found: C, 62.76; H, 7.81; N, 12.10.

EXAMPLE 15

Ethyl 5-[6-(4-acetyl-3-hydroxy-2-(n-propyl)phenoxy)hexyl]-2H-tetrazole-2-(4-butanoate) and the corresponding 1H-1-tetrazole isomer In a procedure similar to that of Example 12, the following reagents and amounts were combined:
potassium carbonate (1.45 g, 10.5 mmol);
potassium iodide (1.75 g, 10.5 mmol);
MEK (100 ml); 5-[6-(4-acetyl-3-hydroxy-2-(n-propyl)-phenoxy)hexyl]-2H-tetrazole (3.47 g, 10.0 mmol); and
ethyl 4-bromobutanoate (1.7 ml, 11 mmol).

The resultant reaction mixture was stirred at reflux temperature overnight and a standard work-up procedure was done to the point where the resultant crude residue was partitioned between ethyl acetate (200 ml) and water (50 ml). The organic phase was dried and concentrated in the usual manner. The crude product was flash chromatographed (Kieselgel® 60, 230–400 mesh, 7.5 cm (dia) by 15 cm (length)) eluted with first 35% ethyl acetate in hexane (3 l) then with a 1:1 ethyl acetate:hexane mixture to yield 2.39 g, 52% of ethyl 5-[6-(4-acetyl-3-hydroxy-2-(n-propyl)phenoxy)hexyl]-2H-tetrazole-2-(4-butanoate) and 1.60 g, 35% of the corresponding 1H-1-tetrazole isomer. 2H-2-Tetrazole isomer of the title product: n.m.r. (300 MHz, CDCl$_3$) δ: 12.74 (s, 1H); 7.58 (d, 1H); 6.42 (d, 1H); 4.64 (t, 2H); 4.14 (q, 2H); 4.02 (t, 2H); 2.90 (t, 2H); 2.62 (t, 2H); 2.56 (s, 3H); 2.34 (m, 4H); 1.82 (m, 4H); 1.53 (m, 6H); 1.26 (t, 3H); 0.93 (t, 3H).

Analysis calculated for C$_{24}$H$_{36}$N$_4$O$_5$: Theory: C, 62.59; H, 7.88; N, 12.16; Found: C, 62.29; H, 8.02; N, 11.89.

1H-1-Tetrazole isomer of the title product: n.m.r. (300 MHz, CDCl$_3$) δ: 12.74 (s, 1H); 7.58 (d, 1H); 6.42 (d, 1H); 4.35 (t, 2H); 4.13 (q, 2H); 4.02 (t, 2H); 2.87 (t, 2H); 2.62 (t, 2H); 2.56 (s, 3H); 2.40 (t, 2H); 2.22 (m, 2H); 1.86 (m, 4H); 1.53 (m, 6H); 1.26 (t, 3H); 0.92 (t, 3H).

EXAMPLE 16

Ethyl 5-[6-(4-acetyl-3-hydroxy-2-(n-propyl)-phenoxy)hexyl]-2H-tetrazole-2-(5-pentanoate) and the corresponding 1H-1-tetrazole isomer This example was run under a procedure very similar to that of Example 15 using the following reagents and amounts:

potassium carbonate (1.40 g, 10.4 mmol);
potassium iodide (1.76 g, 10.6 mmol);
MEK (100 ml);
ethyl 5-bromopentanoate (1.65 ml, 10.3 mmol); 5-[6-(4-acetyl-3-hydroxy-2-(n-propyl)phenoxy)hexyl]-2H-tetrazole (3.47 g, 10.0 mmol).

This reaction mixture was stirred at reflux temperature for 2.5 hours then at room temperature overnight. The reaction mixture was worked up and chromatographed as in Example 15 to yield 2.74 g, 58% of ethyl 5-[6-(4-acetyl-3-hydroxy-2-(n-propyl)phenoxy)hexyl]-2H-tetrazole-2-(5-pentanoate) and 1.34 g, 28% of the corresponding 1H-1-tetrazole isomer: 2H-2-tetrazole isomer of the title product: n.m.r. (300 MHz, CDCl$_3$) δ: 12.74 (s, 1H); 7.58 (d, 1H); 6.42 (d, 1H); 4.57 (t, 2H); 4.12 (q, 2H); 4.02 (t, 2H); 2.90 (t, 2H); 2.62 (t, 2H); 2.56 (s, 3H); 2.34 (t, 2H); 2.04 (m, 2H); 1.82 (m, 4H); 1.66 (m, 2H); 1.51 (m, 6H); 1.24 (t, 3H); 0.93 (t, 3H).

Analysis calculated for $C_{25}H_{38}N_4O_5$: Theory: C, 63.27; H, 8.07; N, 11.81; Found: C, 63.53; H, 8.29; N, 12.04.

1H-1-tetrazole isomer of the title product: n.m.r. (300 MHz, CDCl$_3$) δ: 12.73 (s, 1H); 7.58 (d, 1H); 6.42 (d, 1H); 4.25 (t, 2H); 4.12 (q, 2H); 4.02 (t, 2H); 2.83 (t, 2H); 2.62 (t, 2H); 2.56 (s, 3H); 2.35 (t, 2H); 1.91 (m, 6H); 1.69 (m, 2H); 1.53 (m, 6H); 1.24 (t, 3H); 0.92 (t, 3H).

Analysis calculated for $C_{25}H_{38}N_4O_5$: Theory: C, 63.27; H, 8.07; N, 11.81; Found: C, 63.51; H, 8.27; N, 11.96.

EXAMPLE 17

5-[4-(4-Acetyl-3-hydroxy-2-(n-propyl)phenoxy)butyl]-2-(α-bromo-α'-p-xylyl)-2H-tetrazole and the corresponding 1H-1-tetrazole isomer In a procedure similar to that of Example 15, the following reagents and amounts were combined:
potassium carbonate (4.17 g, 30.2 mmol);
potassium iodide (5.03 g, 30.3 mmol);
MEK (300 ml);
α,α'-dibromo-p-xylene (20.0 g, 74.3 mmol); and
5-[4-(4-acetyl-3-hydroxy-2-(n-propyl)phenoxy)butyl]-2H-tetrazole (9.55 g, 30.0 mmol).

The reaction mixture was stirred at reflux temperature for 1.5 hours and then at room temperature overnight. The cooled reaction mixture was filtered, concentrated, partitioned, separated, and concentrated in the usual manner. The resultant crude product was chromatographed on preparatory-scale HPLC (silica gel) eluted with a gradiant of a 1:3 mixture to a 1:1 mixture and ethyl acetate:hexane. The product-containing fractions were recombined and chromatographed by flash chromatography (Kieselgel 60, 230–400 mesh, 7.5 cm (dia) by 15 cm (length)) using the following step gradient: 1:3 ethyl acetate:hexane (2 l), 30% ethyl acetate in hexane (1 l), 35% ethyl acetate in hexane (2 l) - (first regioisomer comes off) - 40% ethyl acetate in hexane (1 l), 1:1 ethyl acetate:hexane, etc. This additional chromatography step yielded 2.85 g, 19% of 5-[4-(4-acetyl-3-hydroxy-2-(n-propyl)phenoxy)butyl]-2-(α-bromo-α'-p-xylyl)-2H-tetrazole: m.p. 85°–88° C; 2H-2-tetrazole isomer of the title product: n.m.r. (300 MHz, CDCl$_3$) δ: 12.74 (s, 1H); 7.58 (d, 1H); 7.39 (m, 4H); 6.40 (d, 1H); 5.70 (s, 2H); 4.46 (s, 2H); 4.05 (t, 2H); 2.97 (t, 2H); 2.60 (t, 2H); 2.56 (s, 3H); 1.99 (m, 2H); 1.91 (m, 2H); 1.51 (m, 2H); 0.91 (t, 3H).

Analysis calculated for $C_{24}H_{29}BrN_4O_3$: Theory: C, 57.49; H, 5.83; N, 11.17; Found: C, 57.25; H, 5.92; N, 11.06.

EXAMPLE 18

5-[4-(4-Acetyl-3-hydroxy-2-(n-propyl)phenoxy)butyl]-2-(ethyl-4-methylene(salicylate)-2H-tetrazole In a procedure similar to that of Example 15, the following reagents and amounts were combined:
potassium carbonate (3.45 g, 25.0 mmol);
ethyl 4-(bromomethyl)(acetylsalicylate); (7.60 g, 25.2 mmol);
MEK (200 ml); and
5-[4-(4-acetyl-3-hydroxy-2-(n-propyl)phenoxy)butyl]-2H-tetrazole (7.95 g, 25.0 mmol).

This mixture was stirred and heated to reflux temperature for 17 hours. The reaction mixture was then cooled to room temperature, filtered, and the filtrate was concentrated under reduced pressure. The concentrated filtrate was chromatographed on preparatory-scale HPLC (silica gel) eluted with a gradient of 1:3 to 1:1 ethyl acetate:hexane (4 l) followed by an additional amount (4 l) of 1:1 ethyl acetate:hexane. The two regioisomers were obtained along with mixtures of the free hydroxy analogs. Specifically, the free hydroxy analog of the 2H-2-tetrazole was obtained. Also, a 16% yield, 1.95 g of the free hydroxy 1H-1-tetrazole isomer was obtained. Mixtures of the free and protected hydroxy derivatives of the 2H-2-tetrazole compound (4.8 g, approximately 36% yield) and the free and acylated hydroxy derivatives of the 1H-1-tetrazole isomer (3.1 g, approximately 25%) were also obtained. 2H-2-tetrazole isomer of the title product: n.m.r. (300 MHz, CDCl$_3$) δ: 12.73 (s, 1H); 10.90 (s, 1H); 7.84 (d, 1H); 7.58 (d, 1H); 6.90 (s, 1H); 6.80 (d, 1H); 6.41 (d, 1H); 5.69 (s, 2H); 4.40 (q, 2H); 4.05 (t, 2H); 2.98 (t, 2H); 2.61 (t, 2H); 2.56 (s, 3H);.2.00 (m, 2H); 1.91 (m, 2H); 1.51 (m, 2H); 1.40, (t, 3H); 0.91 (t, 3H).

Analysis calculated for $C_{28}H_{34}N_4O_7$: Theory: C, 62.89; H, 6.50; N, 11.28; Found: C, 62.65; H, 6.48; N, 11.10.

EXAMPLE 19

5-[4-(4-Acetyl-3-hydroxy-2-(n-propyl)phenoxy)butyl]-2-(ethyl 4-methylene-3-acetoxybenzoate)-2H-tetrazole and the corresponding 1H-1-tetrazole isomer In a procedure similar to that of Example 18, the following reagents and amounts were combined:
potassium carbonate (2.76 g, 20.0 mmol);
MEK (200 ml); ethyl 4-(bromomethyl)(3-acetoxy)benzoate (6.68 g, 22.2 mmol); and
5-[4-(4-acetyl-3-hydroxy-2-(n-propyl)phenoxy)butyl]-2H-tetrazole (6.37 g, 20.0 mmol);

This mixture was stirred and heated to reflux temperature for 2.5 hours, the reaction mixture was worked up and chromatographed as in Example 18 except that an additional 3:2 ethyl acetate:hexane (2 l) elution of the HPLC column was carried out at the end of the chromatography procedure. Through this procedure 5.8 g, 54% of 5-4-(4-acetyl-3-hydroxy-2-(n-propyl)phenoxy)butyl]-2-(ethyl 4-methylene-3-acetoxybenzoate)2H-tetrazole was obtained, along with 4.4 g, 41% of the corresponding 1H-1-tetrazole isomer: 2H-2-tetrazole isomer of the title product: n.m.r. (300 MHz, CDCl$_3$) δ: 12.73 (s, 1H); 7.94 (d, 1H); 7.79 (s, 1H); 7.58 (d, 1H); 7.46 (d, 1H); 6.40 (d, 1H); 5.72 (s, 2H); 4.37 (q, 2H); 4.04 (t, 2H); 2.94 (t, 2H); 2.61 (t, 2H); 2.56 (s, 3H); 2.35 (s, 3H); 1.94

(m, 2H); 1.87 (m, 2H); 1.50 (m, 2H); 1.37 (t, 3H); 0.90 (t, 3H).

1H-1-tetrazole isomer of the title product: n.m.r. (300 MHz, CDCl$_3$) δ: 12.73 (s, 1H); 7.90 (d, 1H); 7.79 (s, 1H); 7.59 (d, 1H); 7.11 (d, 1H); 6.37 (d, 1H); 5.52 (s, 2H); 4.37 (q, 2H); 3.97 (t, 2H); 2.74 (t, 2H); 2.62 (t, 2H); 2.57 (s, 3H); 2.35 (s, 3H); 1.86 (m, 4H); 1.49 (m, 2H); 1.38 (t, 3H); 0.90 (t, 3H).

Analysis calculated for $C_{28}H_{34}N_4O_7$: Theory C, 62.44; H, 6.36; N, 10.40; Found: C, 62.16; H, 6.46; N, 10.23.

EXAMPLE 20

5-[4-(4-Acetyl-3-hydroxy-2-(n-propyl)phenoxy)butyl]-2-(α-cyano-α'-p-xylyl)-2H-tetrazole Under a nitrogen atmosphere, the dry DMSO (25 ml), 5-[4-(4-acetyl-3-hydroxy-2-(n-propyl)phenoxy)-butyl]-2H-2-(α-bromo-a'-p-xylyl)-tetrazole (1.40 g, 2.79 mmol), and sodium cyanide (0.144 g, 2.88 mmol) were combined, heated to approximately 60° C. and stirred at this temperature for 6.5 hours. The reaction solution was then permitted to cool to room temperature and stayed at room temperature overnight. The reaction solution was added to water (200 ml) and then extracted with ethyl acetate (200 ml). The organic phase was washed with brine, dried over magnesium sulfate, and concentrated under reduced pressure to a yellow oil. The oil began to crystallize after allowing it to stand for some time at room temperature. The oil was fully recrystallized from an ether/hexane mixture, scratching the side of the flask to induce crystallization and placing it in the refrigerator for approximately 2 hours. The crystals were collected by suction filtration and dried in the same manner to leave 0.80 g, 64% of 5-4-(4-acetyl-3-hydroxy-2-(n-propyl)phenoxy)-butyl]-2-(ethyl α-cyano-α'-p-xylyl)-2H-tetrazole as a crystalline white solid: m.p. 72°-73° C; 2H-2-Tetrazole isomer of the title product: n.m.r. (300 MHz, CDCl$_3$) δ: 12.73 (s, 1H); 7.58 (d, 1H); 7.38 (m, 4H); 6.42 (d, 1H); 5.72 (s, 2H); 4.05 (t, 2H); 3.74 (s, 2H); 2.94 (t, 2H); 2.64 (t, 2H); 2.56 (s, 3H); 2.00 (m, 2H); 1.90 (m, 2H); 1.52 (m, 2H); 0.92 (t, 3H).

Analysis calculated for $C_{25}H_{29}N_5O_3$:
Theory: C, 67.09; H, 6.53; N, 15.65;
Found: C, 67.37; H, 6.63; N, 15.46.

EXAMPLE 21

5-[para-(4-Acetyl-3-hydroxy-2-(n-propyl)phenoxy)]-phenyl]-2-[p-cyanobenzyl]-2H-tetrazole and the corresponding 1-substituted-1H-tetrazole isomer Under a nitrogen atmosphere, 5-[para-(4-acetyl-3-hydroxy-2-(n-propyl)phenyl]-2H-tetrazole (0.80 g, 2.4 mmol), α-bromo-p-tolunitrile (0.50 g, 2.6 mmol), potassium carbonate (0.35 g, 2.5 mmol) and MEK (25 ml) were combined. The reaction mixture was stirred and heated to reflux temperature for 2.5 hours then allowed to cool to room temperature and filtered. The filtrate was concentrated in vacuo. The resultant residue was flash chromatographed (Kieselgel® 60, 230-400 mesh, 4 cm dia. × 17 cm length) eluted isocratically with 30% ethyl acetate in hexane. The fractions containing the 2-substituted-2H-tetrazole isomer were concentrated in vacuo to give 0.45 g of an oil of this isomer. The oil crystallized upon standing, then was recrystallized from an ether/hexane mixture to give 0.33 g, 30% of the 2-substituted-2H isomer of the title product: m.p. 114°-115° C.; n.m.r. (300 MHz, CDCl$_3$) δ: 12.91 (s, 1H); 8.12 (d, 2H); 7.70 (d, 2H); 7.53 (m, 3H); 7.10 (d, 2H); 6.38 (d, 1H); 5.87 (s, 2H); 2.74 (t, 2H); 2.59 (s, 3H); 1.62 (m, 2H); 0.96 (t, 3H).

Analysis calculated for $C_{26}H_{23}N_5O_3$:
Theory: C, 68.86; H, 5.11; N, 15.44;
Found: C, 69.08; H, 5.32; N, 15.56.

EXAMPLE 22

5-[para-(4-Acetyl-3-hydroxy-2-(n-propyl)phenoxy)-phenyl]-2-[1-cyanoprop-3-yl]-2H-tetrazole and the corresponding 1-substituted-1H-tetrazole isomer Under a nitrogen atmosphere, 5-[para-(4-acetyl-3-hydroxy-2-(n-propyl)phenoxy)phenyl]-2H-tetrazole (1.00 g, 2.96 mmol), potassium carbonate (0.41 g, 3.0 mmol), potassium iodide (0.54 g, 3.3 mmol), 4-bromobutyronitrile (0.35 ml, 3.4 mmol), and MEK (50 ml) were combined. The reaction mixture was stirred and heated to reflux temperature for 4 hours and 45 minutes. The reaction mixture was allowed to cool to room temperature, diluted with ethyl acetate (250 ml) and the organic phase washed with water (50 ml) and brine (50 ml). The phases were separated and the organic phase stood at room temperature overnight. The organic phase was dried over magnesium sulfate, filtered, and concentrated in vacuo to yield 1.7 g of an oil. The oil was flash chromatographed (Kieselgel® 60, 230-400 mesh, 4 cm dia×15 cm length) eluted isocratically with a mixture of 1:1 ethyl acetate:hexane. The fractions containing the two isomers were combined separately and concentrated in vacuo. 2H-2-tetrazole isomer of the title product: n.m.r. (300 MHz, CDCl$_3$) δ: 12.94 (s, 1H); 8.15 (d, 2H); 7.58 (d, 1H); 7.12 (d, 2H); 6.38 (d, 1H); 4.83 (t, 2H); 2.72 (t, 2H); 2.60 (s, 3H); 2.54 (m, 2H); 2.46 (m, 2H); 1.58 (m, 2H); 0.97 (t, 3H).

EXAMPLE 23

5-[3-(4-Acetyl-3-hydroxy-2-(n-propyl)phenoxy) propyl]-2-[ethyl pentanoate]-2H-tetrazole and the corresponding 1-substituted-1H-tetrazole isomer Under a nitrogen atmosphere, 5-[3-(4-acetyl-3-hydroxy-2-(n-propyl)phenoxy)propyl]-2H-tetrazole (2.00 g, 6.57 mmol), potassium carbonate (0.91 g, 6.6 mmol), potassium iodide (1.09 g, 6.57 mmol), and MEK (75 ml) were combined and stirred at room temperature. Ethyl 5-bromopentanoate (1.16 ml, 7.26 mmol) was added and the reaction mixture was stirred and heated to reflux temperature for 5 hours. The reaction mixture was stirred overnight at room temperature and filtered. The filtrate was concentrated under reduced pressure. The resultant residue was partitioned between ethyl acetate (100 ml) and 5% aqueous sodium bicarbonate solution (30 ml). The phases were separated. The organic phase was washed with water (30 ml) and brine (30 ml), dried over magnesium sulfate, filtered, and concentrated in vacuo to yield 3.68 g of a yellow oil. the oil was flash chromatographed (Keiselgel® 60, 230-400 mesh, 4 cm dia. × 15 cm length) eluted isocratically with a 1:1 mixture of ethyl acetate:hexate. The fractions containing the two isomers were combined separately and reduced in vacuo to give 2.31 g, 81% of the 2H-tetrazole isomer of the title product and 0.7 g of the 1H-tetrazole isomer: 2H-2-Tetrazole isomer of the title product: n.m.r. (300 MHz, CDCl$_3$) δ: 12.76 (s, 1H); 7.58 (d, 1H); 6.44 (d, 1H); 4.58 (t, 2H); 4.13 (m, 4H); 3.11 (t, 2H); 2.64 (t, 2H); 2.56 (s, 3H); 2.35 (m, 4H); 2.05 (m, 2H); 1.66 (m, 2H); 1.55 (m, 2H); 1.25 (t, 3H); 0.94 (t, 3H).

1H-1-Tetrazole isomer of the title product: n.m.r. (300 MHz, CDCl$_3$) δ: 12.75 (s, 1H): 7.60 (d, 1H); 6.42 (d, 1H): 4.27 (t, 2H): 4.17 (t, 2H); 4.12 (q, 2H): 3.06 (t, 2H): 2.64 (t, 2H): 2.57 (s, 3H); 2.43 (m, 2H); 2.31 (t, 2H); 1.94 (m, 2H): 1.63 (m, 2H); 1.58 (m, 2H): 0.95 (t, 3H).

Analysis calculated for $C_{22}H_{23}N_5O_3$: Theory: C, 61.09; H, 7.46; N, 12.95; Found: C, 61.20; H, 7.57; N, 12.82.

EXAMPLE 23A

5-[4-(4-Acetyl-3-hydroxy-2-(n-propyl)phenoxy)butyl]-2[4-(1H-tetrazol-5-yl)butyl]-2H-tetrazole Under a nitrogen atmosphere, 5-[4-acetyl-3-hydroxy-2-(n-propyl)phenoxy)butyl]-2H-2-(5-valeronitrile)tetrazole (4.04 g, 10.1 mmol), tris (n-butyl)tin azide (9.6 ml, 36 mmol), and DME (15 ml) were combined. The reaction solution was stirred at reflux temperature for two days. The mixture was allowed to cool to room temperature; then methanol (50 ml) and 1N hydrochloric acid (40 ml) were added. The mixture was stirred at room temperature for 3.5 hours, then partitioned between ethyl acetate (250 ml) and water (50 ml). The phases were separated and the organic phase was washed with brine (50 ml), dried over magnesium sulfate, filtered, and concentrated under reduced pressure. The resultant residue was chromatographed on a preparatory scale HPLC (silica column), eluted with a gradient of a mixture of 30% ethyl acetate in hexane plus 1% acetic acid (2 l) to a mixture of 60% ethyl acetate in hexane plus 1% acetic acid (2 l). The column was then eluted isocratically first with a mixture of 60% ethyl acetate in hexane plus 1% acetic acid (4 l) then 70% ethyl acetate in hexane plus 1% acetic acid. The product-containing fractions were combined and concentrated in vacuo. The residue was dissolved in the minimum amount of hot diethyl ether (approximately 400 ml, concentrated to approx. 130 ml). The ether solution was allowed to cool to room temperature, at which time seed crystals from the boiling sticks were added. The crystals were allowed to form for one hour at room temperature then refrigerated. The crystals were collected by filtration to yield 2.98 g, 67% 5-[4-(4-acetyl-3-hydroxy-2-(n-propyl)phenoxy)butyl]-2-4-(1H-tetrazol-5-yl)butyl]-2H-tetrazole: m.p. 79°–80° C.; n.m.r. (300 MHz, CDCl$_3$) δ: 12.75 (s, 1H); 7.58 (d, 1H); 6.42 (d, 1H); 4.64 (t, 2H); 4.07 (t, 2H); 3.10 (t, 2H); 3.00 (t, 2H); 2.60 (t, 2H); 2.56 (s, 3H); 2.14 (m, 2H); 2.01 (m, 2H); 1.92 (m, 4H); 1.50 (m, 2H); 0.89 (t, 3H).

Analysis calculated for $C_{21}H_{30}N_8O_3$: Theory: C, 57.00; H, 6.83; N, 25.32; Found: C, 56.75; H, 6.73; N, 25.16.

EXAMPLE 24

5-4-(4-Acetyl-3-hydroxy-2-(n-propyl)phenoxy)butyl]-1H-tetrazole-1-[5-pentanoic acid]

Ethyl 5-4-(4-acetyl-3-hydroxy-2-(n-propyl) phenoxy)butyl]-1H-tetrazole-1-(5-pentanoate) (3.3 g, 7.4 mmol) and absolute ethanol (100 ml) were combined and stirred. 4N potassium hydroxide solution (17 ml) was added and the solution was stirred at room temperature for 1.5 hours. The pH of the reaction solution was adjusted to 1.9 by the addition of 6N hydrochloric acid (11 ml). The reaction mixture was concentrated in vacuo to remove the ethanol. The concentrate was partitioned ethyl acetate (100 ml) and deionized water (40 ml). The phases were separated and the organic phase was washed with brine, dried over magnesium sulfate, filtered, and concentrated under reduced pressure to yield a dark yellow oil. The oil crystallized upon standing at room temperature. The crystals were recrystallized from a mixture of ethyl acetate and hexane to yield 2.1 g, 68% yield of 5-[4-(4-acetyl-3-hydroxy-2-(n-propyl)phenoxy)butyl]-1H-tetrazole-1-[5-pentanoic acid]: m.p. 103°–104° C; n.m.r. (300 MHz, CDCl$_3$) δ: 12.75 (s, 1H); 7.58 (d, 1H); 6.44 (d, 1H); 4.26 (t, 2H); 4.08 (t, 2H); 2.92 (t, 2H); 2.60 (t, 2H); 2.55 (s, 3H); 2.40 (t, 2H); 2.07 (m, 2H); 1.98 (m, 4H); 1.66 (m, 2H); 1.51 (m, 2H); 0.90 (t, 3H).

Analysis calculated for $C_{21}H_{30}N_4O_5$: Theory: C, 60.27; H, 7.23; N, 13.39; Found: C, 60.04; H, 6.96; N, 13.31.

EXAMPLE 25

5-[4-(4-Acetyl-3-hydroxy-2-(n-propyl)phenoxy)butyl]-2-3-(1H-tetrazol-5-yl)propyl]-2H-tetrazole Under a nitrogen atmosphere, 5-4-(4-acetyl-3-hydroxy-2-(n-propyl)phenoxy)butyl]-2-(4-butyronitrile)-2H-tetrazole (7.51 g, 19.5 mmol), DME (40 ml), and tris (n-butyl)tin azide (16 ml, 60 mmol) were combined. The reaction mixture was stirred and heated to reflux temperature for five days. The reaction solution was permitted to cool then diluted with methanol (65 ml); then 1N hydrochloric acid (65 ml) was added. The acidified mixture was stirred for one hour at room temperature then concentrated under reduced pressure. The residue was subjected to preparatory-scale HPLC (silica column) eluted with a gradient of a mixture of 1:3 ethyl acetate to hexane plus 1% acetic acid (4 l) to 1:1 ethyl acetate to hexane plus 1% acetic acid (4 l). The gradient elution was followed by isocratic elution with additional 1:1 ethyl acetate:hexane plus 1% acetic acid (2 l) to yield 8.9 g of oil. The oil was flash chromatographed (Kieselgel ® 60, 230–400 mesh, 4 cm dia. × 14 cm length) eluting with a mixture of 3:1 ethyl acetate:hexane plus 1% acetic acid, to yield (after concentration in vacuo) 8 g of an oil. Crystallization from ether yielded a first crop of 1.12 g, 13% of the title product, (m.p. 74°–77° C.) and 3.7 g, 44% as a second crop of the title product, (m.p. 76°–78° C.); n.m.r. (300 MHz, CDCl$_3$) δ: 12.75 (s, 1H); 7.58 (d, 1H); 6.42 (d, 1H); 4.70 (t, 2H); 4.08 (t, 2H); 3.03 (m, 4H) (overlapping triplets); 2.58 (m, 4H); 2.57 (s, 3H); 2.02 (m, 2H); 1.93 (m, 2H); 1.51 (m, 2H); 0.90 (t, 3H).

Analysis Calculated for $C_{20}H_{28}N_8O_3$: Theory: C, 56.06; H, 6.59; N, 26.15; Found: C, 56.11; H, 6.67; N, 25.90.

EXAMPLE 26

5-4-(4-Acetyl-3-hydroxy-2-(n-propyl)phenoxybutyl]-2-[6-(1H-tetrazol-5-yl)hexyl]-2H-tetrazole Under a nitrogen atmosphere, 5-[4-(4-acetyl-3-hydroxy-2-(n-propyl)phenoxy)butyl]-2-(7-heptanonitrile)-2H-tetrazole (5.5 g, 12.9 mmol), tris(n-butyl)tin azide (10 ml, 37.3 mmol), and DME (15 ml) were combined. The reaction mixture was stirred and heated to reflux temperature for 6 days then permitted to cool to room temperature. The reaction solution was diluted with methanol (50 ml) and acidified with 1N hydrochloric acid (40 ml). The acidified mixture was stirred at room temperature overnight.

The reaction mixture was concentrated under reduced pressure. The concentrate was subjected to preparatory-scale HPLC (silica column) eluted with a gradient of 40% ethyl acetate in hexane plus 1% acetic acid (4 l) to 70% ethyl acetate in hexane plus 1% acetic acid (4 l) and then an isocratic elution with the latter solvent mixture (3 l). The product-containing fractions were combined, concentrated and stored in vacuo overnight.

The concentrate was dissolved in the minimum amount of hot ether. The solution was allowed to cool to room temperature and the resultant solution was decanted from the sediment. The ether solution was cooled to 0° C. and the crystals that precipitated were collected by filtration to yield 2.15 g, 35% of 5-4-(4-acetyl-3-hydroxy-2-(n-propyl)phenoxy-butyl]-2-[6-(1H-tetrazol-5-yl)hexyl]-2H-tetrazole: m.p. 86°–88° C.; n.m.r. (300 MHz, CDCl$_3$) δ: 12.77 (s, 1H); 7.58 (d, 1H); 6.42 (d, 1H); 4.56 (t, 2H); 4.07 (t, 2H); 3.00 (m, 4H); 2.61 (t, 2H); 2.57 (s, 3H); 1.97 (m, 8H); 1.45 (m, 6H); 0.90 (t, 3H).

Analysis calculated for $C_{23}H_{34}N_8O_3$: Theory: C, 58.71; H, 7.28; N, 23.81; Found: C, 58.95; H, 7.49; N, 23.98.

EXAMPLE 27

5-[4-(4-Acetyl-3-hydroxy-2-propylphenoxy)butyl]-2H-tetrazole-2-(7-heptanoic acid)

In a procedure similar to that of Example 29, the following reagents and amounts were combined:
5-[4-(4-Acetyl-3-hydroxy-2-(n-propyl)phenoxy) butyl-2-(7-heptanonitrile)-2H-tetrazole (4.27 g, 9.99 mol);
Absolute ethanol (15 ml); and
2.5N sodium hydroxide solution (80 ml).

These components were stirred overnight at reflux temperature, permitted to cool and stirred at room temperature for 4 days. The reaction mixture was acidified, extracted and flash chromatographed with 1:1 ethyl acetate:hexane plus 1% acetic acid in the usual manner. The product-containing fractions were combined and concentrated under reduced pressure to an oil. The oil began to crystallize upon standing and was recrystallized from ether/hexane with the aid of seed crystals to yield 0.82 g, 18% of a light beige powder of the title product: m.p. 52–55° C; n.m.r. (300 MHz, CDCl$_3$) δ: 12.73 (s, 1H); 7.58 (d, 1H); 6.42 (d, 1H); 4.55 (t, 2H); 4.07 (t, 2H); 2.98 (t, 2H); 2.63 (t, 2H); 2.57 (s, 3H); 2.35 (t, 2H); 2.00 (m, 4H); 1.93 (m, 2H); 1.63 (m, 2H); 1.52 (m, 2H); 1.37 (m, 4H); 0.92 (t, 3H).

Analysis calculated for $C_{23}H_{34}N_4O_5$:
Theory: C, 61.86: H, 7.67; N, 12.55;
Found: C, 61.60; H, 7.87; N, 12.50.

EXAMPLE 28

5-[4-(4-Acetyl-3-hydroxy-2-(n-propyl)phenoxy)butyl]-2-[5-(1H-tetrazol-5-yl)pentyl]-2H-tetrazole In a manner similar to Example 25, the title compound was prepared using the following reaction conditions:
5-4-(4-acetyl-3-hydroxy-2-(n-propyl)phenoxy)butyl]-2-(6-hexanonitrile)-2H-tetrazole (4.53 g, 11.0 mmol)
Tris(n-butyl)tin azide: (10.0 ml, 37.3 mmol)
DME: (15 ml)
Reflux time: 2 Days
Methanol: (50 ml)
1N HCl: (40 ml)
Stir time, temperature: 1.5 hours at room temperature
HPLC
Column: Silica Gradient eluant:
40% EA in hexane plus 1% HOAc (4 l) to 70% EA in hexane plus 1% HOAc (4 l);

Isocratic eluant:
70% EA in hexane plus 1% HOAc (2 l);
75% EA in hexane plus 1% HOAc (3 l);
Crystallization: From ether to give oil, oil stored in refrigeratior overnight, crystallized
Yield: 2.65 g, 53%
m.p.: 79°–82° C.
n.m.r. (300 MHz, CDCl$_3$) δ: 12.74 (s, 1H); 7.58 (d, 1H); 6.42 (d, 1H); 4.58 (t, 2H); 4.07 (t, 2H); 3.02 (m, 4H); 2.59 (t, 2H); 2.56 (s, 3H); 2.03 (m, 4H); 1.91 (m, 4H); 1.48 (m, 4H); 0.89 (t, 3H).
Calculated Analysis for $C_{22}H_{32}N_8O_3$: Theory: C, 57.88; H, 7.07; N, 24.54; Found: C, 57.75; H, 6.95; N, 24.32.

EXAMPLE 29

5-[4-(4-Acetyl-3-hydroxy-2-(n-propylphenoxy)butyl]-2H-tetrazole-2-(6-hexanoic acid)

5-[4-(4-Acetyl-3-hydroxy-2-(n-propylphenoxy)-butyl]-2H-2-(6-hexanonitrile) tetrazole (5.03 g 12.2 mmol), absolute ethanol (20 ml), and 2.5 N sodium hydroxide solution, (100 ml) were combined and stirred at reflux temperature overnight. The mixture was acidified with 6N hydrochloric acid (50 ml) then extracted with ethyl acetate (300 ml). The organic layer was washed with brine (50 ml), dried over magnesium sulfate, filtered and concentrated in vacuo to give a brown oil. The brown oil was permitted to stand overnight then flash chromatographed (Kieselgel ® 60, 230–400 mesh, column: 7.5 cm diameter by 15 cm length) eluted 1:1 ethyl acetate:hexane plus 1% acetic acid. The product-containing fractions were combined and concentrated to a yellow oil. The oil was dissolved in a minimum amount of hot ether and hexane was added slowly to the point of cloudiness. The solution was permitted to stand overnight to yield an oil. The oil was again flash chromatographed (same column as above) eluted with a 1:1 ethyl acetate:hexane mixture to elute a higher R$_f$ material and then eluted with a 3:2 ethyl acetate:hexane mixture to give the desired acid. The resultant oil crystallized upon standing and attempted recrystallization from an ether/hexane mixture yielded again an oil. The oil solidified on standing overnight and was washed with a 1:1 ether/hexane mixture to yield 0.62 g, 12% of the title product: m.p. 55°–57° C. n.m.r. (300 MHz, CDCl$_3$) δ: 12.73 (s, 1H); 7.58 (d, 1H); 6.42 (d, 1H); 4.58 (t, 2H); 4.06 (t, 2H); 2.99 (t, 2H); 2.62 (t, 2H); 2.57 (s, 3H); 2.00 (m, 4H); 1.92 (m, 2H); 1.68 (m, 2H); 1.49 (m, 2H); 1.38 (m, 2H); 0.91 (t, 3H).
Calculated Analysis for $C_{20}H_{32}N_4O_5$: Theory: C, 61.09; H, 7.46; N, 12.95; Found: C, 61.24; H, 7.41; N, 12.68.

EXAMPLE 30

5-4-(4-Acetyl-3-hydroxy-2-(n-propyl)phenoxy)butyl]-2-[para-(1H-tetrazol-5-yl)benzyl]-2H-tetrazole In a manner similar to Example 25, the title compound was prepared using the following reaction conditions:
5-[4-(4-acetyl-3-hydroxy-2-(n-propyl)phenoxy)butyl]-2-(p -methylbenzonitrile)-2H-tetrazole (4.34 g, 10.0 mmol)
Tris(n-butyl)tin azide: (10.0 ml, 37.3 mmol)
DME: (12 ml)
Reflux time: 3 days, 15 hours
Methanol: (40 ml)
1N HCl: (40 ml)

Stir time, temperature: 1 hour at room temperature
HPLC:
Column: silica
Gradient eluant:
  30% EA in hexane plus 1% HOAc to
  60% EA in hexane plus 1% HOAc
Crystallization: triturated in hot ether, crystallized from hot ether that gradually cooled to room temperature then to refrigerator
  Yield: 1.62 g, 34%
  m.p.: 127°–129° C.
  n.m.r. (300 MHz, DMSO-$d_6$) δ: 12.84 (s, 1H); 8.05 (d, 2H); 7.79 (d, 1H); 7.56 (d, 2H); 6.62 (d, 1H); 6.00 (s, 2H); 4.10 (t, 2H); 2.94 (t, 2H); 2.58 (s, 3H); 2.51 (t, 2H); 1.84 (m, 4H); 1.42 (m, 2H); 0.91 (t, 3H).
  Elemental Analysis for $C_{23}H_{28}N_8O_3$: Theory: C, 60.49; H, 5.92; N, 23.51; Found: C, 60.48; H, 5.98; N, 23.23.

EXAMPLE 31

5-[4-(4-Acetyl-3-hydroxy-2-propylphenoxy)butyl]-2H-tetrazole-2-(α-methylene-p-benzoic acid)

In a procedure similar to that of Example 27, the following compounds and amounts were combined:
5-[4-(4-Acetyl-3-hydroxy-2-(n-propyl)phenoxy)butyl]-2-(p-methylbenzonitrile)-2H-tetrazole (8.00 g, 18.5 mmol);
Absolute ethanol (25 ml); and
2.5N sodium hydroxide solution (150 ml).

The mixture was stirred and heated to reflux temperature overnight then allowed to cool to room temperature. Upon cooling a yellow precipitate formed. The reaction mixture was filtered and the filtrate was acidified by the addition of 6N hydrochloric acid (70 ml). The acidified filtrate was stirred and the beige solid thus formed were collected by filtration and washed with water. The solid was dissolved in ethyl acetate and filtered. The filtrate was chromatographed by preparatory-scale HPLC (silica column) eluted isocratically with a mixture of 1:1 ethyl acetate:hexane plus 1% acetic acid (4 l). The productcontaining fractions were concentrated. The resultant crystals and mother liquors were further concentrated in vacuo. The residue was recrystallized from ethyl acetate/hexane and permitted to stand at room temperature overnight. The crystallization mixtures were transferred to the refrigerator for several hours. The crystals were collected by suction filtration and dried in the open to give 6.1 g, 73% of the title product: n.m.r. (300 MHz, CDCl$_3$) δ: 12.73 (s, 1H); 8.10 (d, 2H); 7.58 (d, 1H); 7.44 (d, 2H); 6.40 (d, 1H); 5.79 (s, 2H); 4.05 (t, 2H); 2.99 (t, 2H); 2.61 (t, 2H); 2.56 (s, 3H); 1.99 (m, 2H); 1.90 (m, 2H); 1.51 (m, 2H); 0.90 (t, 3H).
Calculated Analysis for $C_{24}H_{28}N_4O_5$: Theory: C, 63.70; H, 6.24; N, 12.38; Found: C, 63.88; H, 6.08; N, 12.20.

EXAMPLE 32

5-[4-(4-Acetyl-3-hydroxy-2-(n-propyl)phenoxy)butyl]-1-[para-(1H-tetrazol-5-yl)benzyl]-1H-tetrazole In a manner similar to Example 25, the title compound was prepared using the following reaction conditions:
5-[4-(4-acetyl-3-hydroxy-2-(n-propyl)phenoxy)butyl]-1-[para-methylenebenzonitrile]-1H-tetrazole (4.50 g, 10.4 mmol)
Tris(n-butyl)tin azide: (10.0 ml, 37.3 mmol)
DME: (15 ml)
Reflux time: 6 days
Methanol: (30 ml)
1N HCl: (40 ml)
Stir time, temperature: several hours at room temperature
HPLC:
Flash Chromatography: Kieselgel ® 60, 230–400 mesh, column: 4 cm dia. × 15 cm length; eluted with a step gradient of the following mixtures (all contained 1% HOAc):
  1:1 EA:hexane (2 l);
  3:2 EA:hexane (2 l);
  7:3 EA:hexane (2 l);
  4:1 EA:hexane (2 l);
The product was obtained as a yellow oil which crystallized upon standing to yield 3.15 g, 64% of the title product: n.m.r. (300 MHz, CDCl$_3$) δ: 12.70 (s, 1H); 8.10 (d, 2H); 7.50 (d, 1H); 7.30 (d, 2H); 6.31 (d, 1H); 5.60 (s, 2H); 3.95 (t, 2H); 2.91 (t, 2H); 2.53 (s, 3H); 2.12 (m, 2H); 1.89 (m, 2H); 1.41 (m, 2H); 0.81 (t, 3H).

EXAMPLE 33

5-[4-(4-Acetyl-3-hydroxy-2-(n-propyl)phenoxy)butyl]-1H-tetrazole-1-[para-methylenebenzoic acid]

In a procedure similar to Example 29, the carboxylic acid title compound was made using the following reaction conditions:
5-[4-(4-acetyl-3-hydroxy-2-(n-propyl)phenoxy)butyl] 1-[para-methylenebenzonitrile]-1H-tetrazole (4.30 g, 9.92 mmol)
Absolute ethanol: (20 ml)
2.5N NaOH: (80 ml)
Reflux time: Overnight
6N HCl: (appropriate amount).
Ethyl acetate (extraction): (appropriate amount)
Flash Chromatrography:
Column: (Kieselgel ® 60, 230–400 mesh, 4 cm dia. × 15 cm length)
Eluant: 1:1 EA:hexane
Crystallization: from ether (approx. 125 ml)
  Yield: 1.8 g, (40%)
  m.p. (After drying) 68°–72° C.
  Title product: n.m.r. (300 MHz, CDCl$_3$) δ: 12.73 (s, 1H); 8.10 (d, 2H); 7.58 (d, 1H); 7.25 (d, 2H); 6.37 (d, 1H); 5.59 (s, 2H); 3.98 (t, 2H); 2.83 (t, 2H); 2.58 (t, 2H); 2.56 (s, 3H); 1.97 (m, 2H); 1.87 (m, 2H); 0.89 (t, 3H).
  Elemental analysis for $C_{24}H_{28}N_4O_5$: Theory: C, 63.70; H, 6.24; N, 12.38; Found: C, 63.91; H, 6.26; N, 12.18.

EXAMPLE 34

5-[4-(4-Acetyl-3-hydroxy-2-(n-propyl)phenoxy)butyl]-2-[meta-(1H-tetrazol-5-yl)benzyl]-2H-tetrazole In a manner similar to Example 25, the title compound was prepared using the following reaction conditions:
5-4-(4-acetyl-3-hydroxy-2-(n-propyl)phenoxyl)butyl] 2-(m-methylbenzonitrile)-2H-tetrazole (4.33 g, 10.0 mmol)
Tris(n-butyl)tin azide: (10.0 ml, 37.3 mmol)
DME: (15 ml)
Reflux time: 2 days (then overnight at room temperature)
Methanol:(50 ml)
1N HCl: (40 ml)
Stir time, temperature: 2.5 hours at room temperature HPLC:
Column: Silica
Gradient eluant: 30% to 60% EA/hexane plus 1% acetic acid
Crystallization: The solid was recrystallized from EA/hexane to give 4.46 g, (94%)
m.p. 123°-124° C.
n.m.r. (300 MHz, CDCl$_3$) δ: 12.74 (s, 1H); 8.24 (m, 2H); 7.60 (m, 3H); 6.39 (d, 1H); 5.86 (s, 2H); 4.05 (t, 2H); 3.04 (t, 2H); 2.56 (m, 5H); 2.01 (m, 2H); 1.91 (m, 2H); 1.47 (m, 2H); 0.86 (t, 3H).

Elemental Analysis for C$_{24}$H$_{28}$N$_8$O$_3$: Theory: C, 60.49; H, 5.92; N, 23.51; Found: C, 60.69; H, 5.98; N, 23.23.

EXAMPLE 35

5-[4-(4-Acetyl-3-hydroxy-2-(n-propyl)phenoxy)butyl]-2H-tetrazole-2-(α-methylene-m-benzoic acid)

In a manner of Example 29, the following components and amounts were combined:
5-[4-(4-Acetyl-3-hydroxy-2-(n-propyl)phenoxy)-butyl]-2-(m-methylbenzonitrile)-2H-tetrazole (4.30 g, 9.92 mmol), absolute ethanol (15 ml), and 2.5N sodium hydroxide solution (80 ml) were combined and the stirred reaction mixture was refluxed overnight. The mixture was acidified and concentrated as usual then partitioned with ethyl acetate (400 ml) and water (in an amount sufficient to dissolve the brown solid that resulted) and the organic phase was treated as usual. The resultant oil was chromatographed in the usual manner. The product-containing fractions were concentrated and allowed to stand overnight, and the resultant seed crystals were collected and set aside. The product crystallized from the concentrated fractions upon the addition of hexane. The mixture was then placed in a refrigerator for several hours to yield 2.76 g, 61% of white crystals of the title product: m.p. 124°-126° C; n.m.r. (300 MHz, CDCl$_3$) δ: 12.73 (s, 1H); 8.12 (m, 2H); 7.56 (m, 3H); 6.41 (d, 1H); 5.79 (s, 2H); 4.05 (t, 2H); 2.99 (t, 2H); 2.61 (t, 2H); 2.55 (s, 3H); 1.99 (m, 2H); 1.90 (m, 2H); 1.51 (m, 2H); 0.90 (t, 3H).

Calculated Analysis for C$_{24}$H$_{28}$N$_4$O$_5$: Theory: C, 63.70; H, 6.24; N, 12.38; Found: C, 63.87; H, 6.21; N, 12.40.

EXAMPLE 36

5-[4-(4-Acetyl-3-hydroxy-2-(n-propyl)phenoxy)butyl]-1-[meta-(1H-tetrazol-5-yl)benzyl]-1H-tetrazole In a manner similar to Example 25, the title compound was prepared using the following reaction conditions:
5-[4-(4-acetyl-3-hydroxy-2-(n-propyl)phenoxy)butyl]1-(meta-methylenebenzonitrile)-1H-tetrazole. (2.16 g, 4.98 mmol)
Tris(n-butyl)tin azide: (5.0 ml, 18.8 mmol)
DME: (8 ml)
Reflux time: Overnight

EXAMPLE 37

5-[4-(4-Acetyl-3-hydroxy-2-(n-propyl)phenoxy)butyl]-1-meta-methylenebenzoic acid]-1H-tetrazole In a procedure similar to Example 29, the carboxylic acid title compound was made using the following reaction conditions:
5-[4-(4-acetyl-3-hydroxy-2-(n-propyl)phenoxy)butyl]-1-meta-methylenebenzonitrile]-1H-tetrazole (2.16 g, 4.98 mmol)
Absolute ethanol: (8.0 ml)
2.5N NaOH: (40 ml)
Reflux time: Overnight
6N HCl: (20 ml)
Ethyl acetate (extraction): 400 ml & 50 ml water
Flash Chromatography:
Column: Kieselgel ® 60, 230–400 mesh, 4 cm dia.×15 cm length
Eluant: 1:1 EA:hexane plus 1% acetic acid
Crystallization: oil
Yield: 2.15 g (95%)
n.m.r. (300 MHz, CDCl$_3$) δ: 12.72 (s, 1H); 8.09 (d, 1H); 7.97 (s, 1H); 7.56 (d, 1H); 7.47 (m, 3H); 6.36 (d, 1H); 5.59 (s, 2H); 3.99 (t, 2H); 2.88 (t, 2H); 2.58 (t, 2H); 2.55 (s, 3H); 1.97 (m, 2H); 1.88 (m, 2H); 1.48 (m, 2H); 0.89 (t, 3H).

EXAMPLE 38

5-5-(4-Acetyl-3-hydroxy-2-(n-propyl)phenoxy)pentyl]-2-[3-(1H-tetrazol-5-yl)propyl]-2H-tetrazole In a manner similar to Example 25, the title compound was prepared using the following reaction conditions:
5-[5-(4-acetyl-3-hydroxy-2-(n-propyl)phenoxy)pentyl]-2-(4-butyronitrile)-2H-tetrazole (1.10 g, 2.75 mmol)
Tris(n-butyl)tin azide: (3.0 ml, 11.2 mmol)
DME: (5 ml)
Reflux time: Overnight (then at room temperature overnight)
Methanol: (20 ml)
1N HCl: (12 ml)
Stir time, temperature: approximately one hour, room temperature
Flash Chromatography: Kieselgel ® 60, 230–400 mesh, column: 4 cm dia.×15 cm length
Isocratic eluant:
1:1 EA:hexane plus 1% HOAc (1 l)
3:2 EA:hexane plus 1% HOAc (2 l)
Crystallization: from ether (at room temperature then, refrigerator temperature); dried in vacuo at room temperature.
Yield: 0.60 g, (49%)
m.p.: 97°-99° C.
n.m.r. (300 MHz, CDCl$_3$) δ: 12.75 (s, 1H); 7.58 (d, 1H); 6.42 (d, 1H); 4.69 (t, 2H); 4.03 (t, 2H); 3.03 (t, 2H); 2.95 (t, 2H); 2.59 (t, 2H); 2.56 (m, 5H); 1.88 (m, 4H); 1.59 (m, 2H); 1.50 (m, 2H); 0.90 (t, 3H).

Elemental Analysis: C$_{21}$H$_{30}$N$_8$O$_3$: Theory: C, 57.00; H, 6.83; N, 25.32; Found: C, 57.22; H, 6.77; N, 25.44.

EXAMPLE 39

5-[5-(Acetyl-3-hydroxy-2-(n-propyl)phenoxy)pentyl]-2-[4-butanoic acid]-2H-tetrazole In a procedure similar to Example 29, the carboxylic acid title compound was made using the following reaction conditions:
5-5-(4-acetyl-3-hydroxy-2-(n-propyl)phenoxy)pentyl]-2-[4-butyronitrile]-2H-tetrazole 1.28 g, 3.20 mmol)
Absolute ethanol: 10 ml
2.5N NaOH: 60 ml
Reflux time: 3.5 hours (and at room temperature overnight)
6N HCl: (appropriate amount)
Ethyl acetate (extraction): (appropriate amount)

Flash Chromatography:
Column: (Kieselgel ® 60, 230–400 mesh, 4 cm×15 cm length)
Eluant: 3:2 hexane:EA plus 1% acetic acid
Crystallizaion: from ether/hexane
  Yield: 0.90 g (67%)
  m.p.: 77°–78° C.
  n.m.r. (300 MHz, CDCl$_3$) δ: 12.73 (s, 1H); 7.58 (d, 1H); 6.42 (d, 1H); 4.67 (t, 2H); 4.03 (t, 2H); 2.93 (t, 2H); 2.61 (t, 2H); 2.56 (s, 2H); 2.43 (m, 2H); 2.33 (m, 2H); 1.88 (m, 4H); 1.55 (m, 4H); 0.92 (t, 3H).
  Elemental Analysis for $C_{21}H_{30}N_4O_5$: Theory: C, 60.27; H, 7.23; N, 13.39; Found: C, 60.08; H, 7.48; N, 13.12.

EXAMPLE 40

5-[5-(4-Acetyl-3-hydroxy-2-(n-propyl)phenoxy)pentyl]-2-[4-(1H-tetrazol-5-yl)butyl]-2H-tetrazole In a manner similar to Example 25, the title compound was prepared using the following reaction conditions:
5-[5-(4-acetyl-3-hydroxy-2-(n-propyl)phenoxy)pentyl]-2-(5-valeronitrile)-2H-tetrazole (2.66 g, 6.43 mmol)
Tris(n-butyl)tin azide: (5.0 ml, 18.7 mmol)
DME: (11 ml)
Reflux time: (3 days)
Methanol: (25 ml)
1N HCl: (20 ml)
Stir time, temperature: Overnight at room temperature
Flash Chromatography:
Column: (Kieselgel ® 60, 230–400 mesh, 4 cm×15 cm length)
Isocratic eluant:
  (a) 1:1 EA:hexane plus 1% HOAc;
  (b) 3:2 EA:hexane plus 1% HOAc.
Crystallization: from ether
  Yield: 1.97 g (67%)
  m.p.: 86°–88° C.
  n.m.r. (300 MHz, CDCl$_3$) δ: 12.76 (s, 1H); 7.58 (d, 1H); 6.42 (d, 1H); 4.64 (t, 2H); 4.04 (t, 2H); 3.08 (t, 2H); 2.95 (t, 2H); 2.59 (t, 2H); 2.57 (s, 3H); 2.14 (m, 2H); 1.87 (m, 6H); 1.59 (m, 2H); 1.49 (m, 2H); 0.89 (t, 3H).
  Elemental Analysis: for $C_{22}H_{32}N_8O_3$ Theory: C, 57.88; H, 7.07; N, 24.54; Found: C, 58.14; H, 7.32; N, 24.25.

EXAMPLE 41

5-[6-(4-Acetyl-3-hydroxy-2-(n-propyl)phenoxy)hexyl]-2-[3-(1H-tetrazol-5-yl)propyl]-2H-tetrazole In a manner similar to Example 25, the title compound was prepared using the following reaction conditions:
5-6-(4-acetyl-3-hydroxy-2-(n-propyl)phenoxy)hexyl]-2-(4-butyronitrile)-2H-tetrazole: (2.83 g, 6.84 mmol)
Tris(n-butyl)tin azide: (5.0 ml, 18.7 mmol)
DME: (15 ml)
Reflux time: (6 days)
Methanol: (30 ml)
1N HCl: (20 ml)
Stir time, temperature: room termperature overnight
Flash Chromatography:
Column: (Kieselgel ® 60, 230–400 mesh, 4 cm×15 cm length)
Isocratic eluant:
  (a) 1:1 EA:hexane plus 1% HOAc;
  (b) 3:2 EA:hexane plus 1% HOAc.
Crystallization: from ether
  Yield: 2.14 g, 69%
  m.p.: 85°–87° C.
  n.m.r. (300 MHz, CDCl$_3$) δ: 12.74 (s, 1H); 7.58 (d, 1H); 6.42 (d, 1H); 4.70 (t, 2H); 4.03 (t, 2H); 3.06 (t, 2H); 2.94 (t, 2H); 2.61 (m, 4H); 2.57 (s, 3H); 1.83 (m, 4H); 1.52 (m, 6H); 0.92 (t, 3H).
  Elemental Analysis: for $C_{22}H_{32}N_8O_3$: Theory: C, 57.88; H, 7.07; N, 24.54; Found: C, 58.09; H, 7.23; N, 24.74.

EXAMPLE 42

5-[6-(4-Acetyl-3-hydroxy-2-(n-propyl)phenoxy)hexyl]-2-[4-(1H-tetrazol-5-yl)butyl]-2H-tetrazole In a manner similar to Example 25, the title compound was prepared using the following reaction conditions:
5-[6-(4-acetyl-3-hydroxy-2-(n-propyl)phenoxy)hexyl]-2-[4-(cyano)butyl]-2H-tetrazole (2.76 g, 6.46 mmol)
Tris(n-butyl)tin azide: (10 ml, 37.4 mmol)
DME: (15 ml)
Reflux time: 4 days
Methanol: (30 ml)
1N HCl: (20 ml)
Stir time, temperature: 1 hour at room temperature
Flash Chromatography: Kieselgel ® 60, eluted with a step gradient of 1:1 and 3:2 EA/hexane, each plus 1% acetic acid
  n.m.r. (300 MHz, CDCl$_3$) δ: 12.74 (s, 1H); 7.58 (d, 1H); 6.42 (d, 1H); 4.63 (t, 2H); 4.02 (t, 2H); 3.09 (t, 2H); 2.91 (t, 2H); 2.60 (t, 2H); 2.56 (s, 3H); 2.13 (m, 2H); 1.86 (m, 6H); 1.49 (m, 6H); 0.91 (t, 3H).

EXAMPLE 43

5-[6-(4-Acetyl-3-hydroxy-2-(n-propyl)phenoxy)hexyl]-1-[4-(1H-tetrazol-5-yl)butyl]-1H-tetrazole In a manner similar to Example 25, the title compound was prepared using the following reaction conditions:
5-[6-(4-acetyl-3-hydroxy-2-(n-propyl)phenoxy)hexyl]-1-(4-cyanobutyl)-1H-tetrazole: (0.70 g, 1.5 mmol)
Tris(n-butyl)tin azide: (4.0 ml, 15 mmol)
DME: (15 ml)
Reflux time: 4 days
Methanol: (20 ml)
1N HCl: (15 ml)
Stir time, temperature: room temperature overnight
Flash Chromatography: Kieselgel ® 60, 230–400 mesh
Step Gradient eluant: as with Example 42.
  n.m.r. (300 MHz, CDCl$_3$) δ: 12.74 (s, 1H); 7.57 (d, 1H); 6.41 (d, 1H); 4.32 (t, 2H); 4.01 (t, 2H); 3.13 (t, 2H); 2.87 (t, 2H); 2.59 (t, 2H); 2.55 (s, 3H); 2.04 (m, 2H); 1.85 (m, 6H); 1.51 (m, 6H); 0.89 (t, 3H).

EXAMPLE 44

5-[4-(4-Acetyl-3-hydroxy-2-propylphenoxy)butyl]-2H-tetrazol-2-(3-propionic acid)

In a procedure similar to that of Example 62, the following reagents and amounts were combined:
Ethyl 5-4-(4-acetyl-3-hydroxy-2-propylphenoxy)butyl]-2H-tetrazole-2-(3-propionate) (2.05 g, 4.90 mol);
Absolute ethanol (75 ml); and
4N Potassium hydroxide solution (10 ml).

These components were stirred for 85 minutes at room temperature. The reaction was handled in the same manner as Example 62 and, after standing overnight, the product oil gave dark green crystals. The oil and the crystals were heated to reflux with several portions of ether. The ether portions were combined and filtered then concentrated on the steam bath. Hexane was added dropwise until a cloudiness resulted in the solution, resulting in a precipitate of green crystals.

The mother liquor from this precipitation was allowed to stand to induce crystallization. The new crystals were recrystallized from an ether/hexane mixture to give 0.63 g, 33% of the pale yellow title product: m.p.: 81°–84° C.; n.m.r. (300 MHz, CDCl$_3$) δ: 12.73 (s, 1H); 7.58 (d, 1H); 6.42 (d, 1H); 4.85 (t, 2H); 4.06 (t, 2H); 3.13 (t, 2H); 2.99 (t, 2H); 2.62 (t, 2H); 2.56 (s, 3H); 2.00 (m, 2H); 1.91 (m, 2H); 1.51 (m, 2H); 0.92 (t, 3H).
Elemental Analysis: for C$_{19}$H$_{26}$N$_4$O$_5$: Theory: C, 58.45; H, 6.71; N, 14.35; Found: C, 58.46; H, 6.43; N, 14.05.

EXAMPLE 45

5-[4-(4-Acetyl-3-hydroxy-2-(n-propyl)phenoxy)butyl]-1H-tetrazole-1-[3-propionic acid]

In a manner similar to that of Example 44, the title carboxylic acid was obtained from the corresponding ethyl ester using the following reaction conditions:
Ethyl 5-[4-(4-acetyl-3-hydroxy-2-(n-propyl)phenoxy)-butyl]-1H-tetrazole-1-(3-propionate) (1.20 g, 2.39 mmol)
4N KOH: (5.0 ml)
Absolute ethanol: (40 ml)
Stir time: 30 minutes
Acidification, 6N HCl: (4.0 ml, 2.3 pH)
Partition:
  Water: (25 ml)
  Ethyl acetate: (75 ml)
Crystallization: the crude product was flash chromatographed (Kieselgel® 60, 230–400 mesh, 5 cm dia.×15 cm length, eluted with 1% acetic acid in ethyl acetate). The product-containing fractions were combined and concentrated in vacuo. The residue was recrystallized EA/hexane.
Yield: 0.32 g (34%)
m.p.: 138°–140° C.
n.m.r. (300 MHz, CDCl$_3$) δ: 12.73 (s, 1H); 7.58 (d, 1H); 6.42 (d, 1H); 4.47 (t, 2H); 4.08 (t, 2H); 3.03 (m, 4H); 2.61 (t, 2H); 2.56 (s, 3H); 2.06 (m, 2H); 1.96 (m, 2H); 1.52 (m, 2H); 0.91 (t, 3H).

EXAMPLE 46

5-[4-(4-Acetyl-3-hydroxy-2-propylphenoxy)butyl]-2H-tetrazol-2-(4-butyric acid)

In a manner similar to that of Example 62, the following reagents and amounts were combined:
Ethyl 5-[4-(4-acetyl-3-hydroxy-2-propylphenoxy]-butyl]-b 2H-tetrazole-2-(4-butanoate) (6.68 g, 15.4 mol);
4N potassium hydroxide solution (30 ml); and
Absolute ethanol (200 ml).

These components were stirred at room temperature for 2 hours and 45 minutes. The reaction mixture was worked up in the usual manner to yield a reddish-brown oil which was permitted to stand at room temperature for 3 days. The oil crystallized upon standing. The crystalline material was recrystallized from an ether/hexane mixture which was stored in the refrigerator. The off-white crystals were collected to yield 4.52 g, 73% of the title product: m.p.: 62°–63° C.; n.m.r. (300 MHz, CDCl$_3$) δ: 12.73 (s, 1H); 7.58 (d, 1H); 6.42 (d, 1H); 4.67 (t, 2H); 4.07 (t, 2H); 2.99 (t, 2H); 2.63 (t, 2H); 2.56 (s, 3H); 2.45 (t, 2H); 2.32 (m, 2H); 2.00 (m, 2H); 1.92 (m, 2H); 1.52 (m, 2H); 0.92 (t, 3H).

Analysis Calculated for C$_{20}$H$_{28}$N$_4$O$_5$: Theory C, 59.39; H, 6.98; N, 13.85; Found: C, 59.12; H, 7.08; N, 13.66.

EXAMPLE 47

5-[4-(4-Acetyl-3-hydroxy-2-(n-propyl)phenoxy)butyl]-1-[4-butanoic acid]-1H-tetrazole In a manner similar to that of Example 44, the title carboxylic acid was obtained from the corresponding ethyl ester using the following reaction conditions:
Ethyl 5-[4-(4-acetyl-3-hydroxy-2-(n-propyl)phenoxy)-butyl]-1H-tetrazole-1-(4-butanoate) (1.11 g, 2.57 mmol);
4N KOH: (5.0 ml
Absolute ethanol: (40 ml)
Stir time: 2.5 hours
Acidification, 6N HCl: (4.0 ml, pH 2.0)
Partition:
  Water: (20 ml)
  Ethyl acetate: (50 ml)
Crystallization: Taken up in hot ether filtered, hexane added until cloudiness to give oil. The oil was mixed with 1:1 hexane:ether, allowed to stand overnight. Resultant solid crystallized from ether/hexane.
Yield: 0.71 g, (68%)
m.p.: 87°–88° C.
n.m.r. (300 MHz, CDCl$_3$) δ: 12.74 (s, 1H); 7.59 (d, 1H); 6.42 (d, 1)H; 4.37 (t, 2H); 4.09 (t, 2H); 2.96 (t, 2H); 2.61 (t, 2H); 2.56 (s, 3H); 2.48 (t, 2H); 2.23 (m, 2H); 2.08 (m, 2H); 1.96 (m, 2H); 1.51 (m, 2H); 0.91 (t, 3H).
Elemental analysis for C$_{20}$H$_{28}$N$_4$O$_5$: Theory: C, 59.39; H, 698; N, 13.85; Found: C, 59.67; H, 6.96; N, 13.82.

EXAMPLE 48

5-[4-(4-Acetyl-3-hydroxy-2-propylphenoxy)butyl]-2H-tetrazol-2-(5-pentanoic acid)

In a procedure similar to that of Example 62, the following reagents and amounts were combined:
Ethyl 5-4-(4-acetyl-3-hydroxy-2-propylphenoxybutyl]-FB 2H-tetrazole-2-(5-pentanoate) (8.68 g, 19.4 mol).
4N potassium hydroxide solution (45 ml, 180 mmol); and
Absolute ethanol (250 ml).

The above reactants were stirred at room temperature for 1.5 hours and worked up in the usual manner to yield a dark yellow oil. The oil was flash chromatographed (Kieselgel® 60, 230–400 mesh, 3:2 EA:hexane plus 1% acetic acid eluant) to recover a yellow oil which was stored in vacuo overnight at 30° C. The oil was crystallized from an ether/hexane mixture to yield 4.29 g, 53% of the title product: m.p.: 70°–72° C.; n.m.r. (300 MHz, CDCl$_3$) δ: 12.73 (s, 1H); 7.58 (d, 1H); 6.42 (d, 1H); 4.59 (t, 2H); 4.07 (t, 2H); 2.98 (t, 2H); 2.62 (t, 2H); 2.56 (s, 3H); 2.41 (t, 2H); 2.06 (m, 4H); 1.92 (m, 2H); 1.67 (m, 2H); 1.52 (m, 2H); 0.92 (t, 3H).
Elemental Analysis for C$_{21}$H$_{30}$N$_4$O$_5$: Theory: C, 60.27; H, 7.23; N, 13.39; Found: C, 60.42; H, 7.15; N, 13.29.

EXAMPLE 49

5-[4-(4-Acetyl-3-hydroxy-2-propylphenoxy)-butyl]-2H-tetrazole-2-(6-hexanoic acid)

In a procedure similar to that of Example 62, the following reagents and amounts were combined:

Ethyl 5-[4-(4-acetyl-3-hydroxy-2-propylphenoxy)-butyl]-2H-tetrazole-2-(6-hexanoate) (7.00 g, 15.2 mmol);
Absolute ethanol (150 ml); and
4N potassium hydroxide (30 ml, 120 mmol).

The components were stirred at room temperature for 1 hour and 40 minutes. The mixture was worked up in the usual manner and the resultant oil was permitted to stand for 24 hours. The oil was then left in vacuo for approximately 1 hour then left to stand. The oil solidified upon standing to give 6.58 g of a white solid. The solid was recrystallized from ether/hexane mixture to yield 4.64 g, 71% of a colorless solid of the title product: m.p. 57°–59° C.; n.m.r. (300 MHz, CDCl$_3$) δ: 12.73 (s, 1H); 7.58 (d, 1H); 6.42 (d, 1H); 4.57 (t, 2H); 4.07 (t, 2H); 2.98 (t, 2H); 2.63 (t, 2H); 2.56 (s, 3H); 2.36 (t, 2H); 2.01 (m, 4H); 1.92 (m, 2H); 1.69 (m, 2H); 1.52 (m, 2H); 1.40 (m, 2H); 0.92 (t, 3H).
Elemental Analysis for $C_{22}H_{32}N_4O_5$: Theory: C, 61.09; H, 7.46; N, 12.95; Found: C, 60.98; H, 7.67; N, 12.96.

EXAMPLE 50

5-6-(4-Acetyl-3-hydroxy-2-(n-propyl)phenoxy)hexyl]-1H-tetrazole-1-[4-butanoic acid]

In a manner similar to that of Example 44, the title carboxylic acid was obtained from the corresponding ethyl ester using the following reaction conditions:
Ethyl 5-6-(4-acetyl-3-hydroxy-2-(n-propyl)phenoxy)-hexyl]-b 1H-tetrazole-1-(4-butanoate) (1.3 g, 2.8 mmol)
4N KOH: (5 ml)
Absolute ethanol: (25 ml)
Stir time: 2 hours
Acidification, 6N HCl: (3 ml, 2.5 pH)
Partition:
  Water: (Enough for solution)
  Ethyl acetate: (75 ml)
Crystallization: crystallized from ether, dried in vacuo at room temperature for 1.5 hours
  Yield: 0.85 g, (70%)
  m.p.: 87°–88° C.
n.m.r. (300 MHz, CDCl$_3$) δ: 12.73 (s, 1H); 7.58 (d, 1H); 6.42 (d, 1H); 4.35 (t, 2H); 4.03 (t, 2H); 2.86 (t, 2H); 2.62 (t, 2H); 2.57 (s, 3H); 2.49 (t, 2H); 2.23 (m, 2H); 1.86 (m, 4H); 1.52 (m, 6H); 0.93 (t, 3H).
Elemental analysis for $C_{22}H_{32}N_4O_5$: Theory: C, 61.09; H, 7.46; N, 12.95; Found: C, 60.85; H, 7.63; N, 13.02.

EXAMPLE 51

5-[6-(4-Acetyl-3-hydroxy-2-(n-propyl)phenoxy) hexyl]-2H-tetrazole-2-[4-butanoic acid]

In a manner similar to that of Example 44, the title carboxylic acid was obtained from the corresponding ethyl ester using the following reaction conditions:
Ethyl 5-[6-(4-acetyl-3-hydroxy-2-(n-propylphenoxy)-hexyl]-2H-tetrazole-2-(4-butanoate) (2.1 g, 4.6 mmol)
4N KOH: (10 ml)
Absolute ethanol: (50 ml)
Stir time: 2 hours
Acidification, 6N HCl: (7 ml, 2.5 pH)
Partition:
  Water: (Enough for solution, then concentrated in vacuo)
  Ethyl acetate: (100 ml)
Crystallization: Oil taken up in carbon tetrachloride, reconcentrated. Recrystallized from ether/hexane. Dried in air
  Yield: 1.43 g, (72%)
  m.p.: 50°–52° C.
n.m.r. (300 MHz, CDCl$_3$) δ: 12.73 (s, 1H); 7.58 (d, 1H); 6.42 (d, 1H); 4.66 (t, 2H); 4.02 (t, 2H); 2.90 (t, 2H); 2.62 (t, 2H); 2.56 (s, 3H); 2.44 (t, 2H); 2.33 (m, 2H); 1.83 (m, 4H); 1.51 (m, 6H); 0.93 (t, 3H).
Elemental analysis for $C_{22}H_{32}N_4O_5$: Theory: C, 61.09; H, 7.46; N, 12.95; Found: C, 61.26; H, 7.47; N, 12.71.

EXAMPLE 52

5-[6-(4-Acetyl-3-hydroxy-2-(n-propyl)phenoxy)hexyl]-1-[5-pentanoic acid]-1H-tetrazole In a manner similar to that of Example 44, the title carboxylic acid was obtained from the corresponding ethyl ester using the following reaction conditions:
Ethyl 5-[6(4-acetyl-3-hydroxy-2-(n-propyl)phenoxy)-hexyl]-1H-tetrazole-1-(5-pentanoate): (0.94 g, 2.0 mmol)
4N KOH: (4 ml)
Absolute ethanol: (20 ml)
Stir time: 1.5 hours
Acidification, 6N HCl: (3 ml, 1.6 pH)
Partition:
  Water: (25 ml)
  Ethyl acetate: (75 ml)
Crystallization: ether
  Yield: 0.72 g, 81%
  m.p.: 77°–78° C.
n.m.r. (300 MHz, CDCl$_3$) δ: 12.74 (s, 1H); 7.59 (d, 1H); 6.42 (d, 1H); 4.26 (t, 2H); 4.03 (t, 2H); 2.84 (t, 2H); 2.62 (t, 2H); 2.56 (s, 3H); 2.42 (t, 2H); 1.98 (m, 2H); 1.85 (m, 4H); 1.67 m, 2H); 1.53 (m, 6H); 0.92 (t, 3H).
Elemental analysis for $C_{23}H_{34}N_4O_5$: Theory: C, 61.86; H, 7.67; N, 12.55; Found C, 61.62; H 7.54; N 12.60.

EXAMPLE 53

5-[6-(4-Acetyl-3-hydroxy-2-(n-propyl)phenoxy)hexyl]-1-[5-pentanoic acid]-2H-tetrazole.

In a manner similar to that of Example 44, the title carboxylic acid was obtained from the corresponding ethyl ester using the following reaction conditions:
Ethyl 5-[6-(4-acetyl-3-hydroxy-2-(n-propyl)phenoxy)-hexyl]-2H-tetrazole-2-(5-pentanoate): (2.50 g, 5.27 mmol)
4N KOH: (10 ml)
Absolute ethanol: (50 ml)
Stir time: 3 hours
Acidification, 6N HCl: (6 ml, 2.5 pH)
Partition:
  Water: (25 ml)
  Ethyl acetate: (75 ml)
Crystallization: oil taken up in carbon tetrachloride, concentrated in vacuo allowed to stand at room temperature:
  Yield: 1.81 G, 77% as a yellow oil
n.m.r. (300 MHz, CDCl$_3$) δ: 12.73 (s, 1H); 7.58 (d, 1H); 6.42 (d, 1H); 4.58 (t, 2H); 4.01 (t, 2H); 2.90 (t, 2H); 2.62 (t, 2H); 2.56 (s, 3H); 2.40 (t, 2H); 2.06 (m, 2H); 1.82 (m, 4H); 1.66 (m, 2H); 1.50 (m, 6H); 0.91, t, 3H.

EXAMPLE 54

5-[4-(4-Acetyl-3-hydroxy-2-(n-propyl)phenoxy)butyl]-2-[para-(methylene-(1H-tetrazol-5-yl)benzyl]-2H-tetrazole In a manner similar to Example 25, the title compound was prepared using the following reaction conditions:
5-[4-(4-Acetyl-3-hydroxy-2(n-propyl)phenoxy)butyl]-2-[4-methylene-1-cyanomethylenephenyl]-2H-tetrazole:
(0.459 g, 1.03 mmol)
Tris(n-butyl)tin azide: (5.0 ml, 19 mmol)
DME: (10 ml)
Reflux time: 5 days
Methanol: (15 ml)
1N HCl: (15 ml)
Stir time, temperature: Overnight at room temperature
Flash Chromatography: (Kieselgel® 60, 230–400 mesh, 4 cm×15 cm length);
Step gradient:
 (*a) 1:1 EA:Hexane (0.5 l);
 (*b) 3:2 EA:Hexane (0.5 l);
 (*c) 7:3 EA:Hexane (0.5 l);
*plus 1% acetic acid
Crystallization: ethyl acetate/hexane
 Yield: 0.38 g (75%)
 m.p.: 128°–129° C.
 n.m.r. consistent with structure;
 Elemental Analysis for $C_{25}H_{30}N_8O_3$: Theory: C, 61.21; H, 6.16; N, 22.84; Found: C, 61.42; H, 6.11; N, 22.63.

EXAMPLE 55

5-[4-(4-Acetyl-3-hydroxyl-2-(n-propyl)phenoxy)butyl]-2H-tetrahydrazole-2-[4-(methylene)salicylic acid]

In a manner similar to that of Example 44, the title hydroxy-substituted carboxylic acid was obtained from the corresponding acetoxy-substituted ethyl ester using the following reaction conditions:
5-[4-(4-acetyl-3-hydroxy-2-(n-propyl)phenoxy)butyl]-2-(ethyl 4-methylene(acetylsalicylate)-2H-tetrazole (3.1 g, 5.8 to 6.2 mmol)
4N KOH: (15 ml)
Absolute ethanol: (75 ml)
Stir time: stirred at reflux temperature for 3 hours
Acidification, 6N HCl: (10 ml)
*Partition:
 Water: (50 ml)
 Ethyl acetate: (250 ml)
*(water was first added to dissolve salt, then concentrate was partitioned)
Crystallization: (a) Preparatory-Scale HPLC (silica column)-gradient of 30% EA:hexane plus 1% HOAc (4 l) to 60% EA:hexane plus 1% HOAc (4 l), then recrystallized from ethyl acetate/hexane.
 Yield: 0.33 g, (12%)
 m.p.: 138°–140° C.
 n.m.r. consistent with structure;
 Elemental analysis for $C_{24}H_{28}N_4O_6$: Theory: C, 61.53; H, 6.02; N, 11.96; Found: C, 61.54; H, 6.26; N, 11.78.

EXAMPLE 56

5-[4-(4-Acetyl-3-hydroxy-2-(n-propyl)phenoxy)butyl]-1H-tetrazole-1-[(4-methylene)-3-hydroxy benzoic acid]

In a manner similar to that of Example 44, the title hydroxy-substituted carboxylic acid was obtained from the acetoxy-substituted corresponding ethyl ester using the following reaction conditions:
Ethyl 5-[4-(4-acetyl-3-hydroxy-2-(n-propyl)phenoxy)-butyl]-1H-tetrazole-1-(4-methylene)-3-acetoxybenzoate): (3.4 g, 6.3 mmol)
4N KOH: (12 mmol)
Absolute ethanol: (100 ml)
Stir time: Overnight
Acidification, 6N HCl: (10 ml)
*Partition:
 Water:
 Ethyl acetate: (200 ml)
*(water was first added to acidified mixture to dissolve salt, filtered and concentrated)
Crystallization:
 (a) preparatory-scale HPLC (silica column): gradient: 30% EA:hexane plus 1% HOAc (2 l) to 3:2 EA:hexane plus 1% HOAc (2 l); (isocratic): 3:2 EA:hexane plus 1% HOAc (4 l).
 (b) Product recrystallized from EA/hexane.
 Yield: 0.85 g, (29%)
 m.p.: 160°–163° C.
 n.m.r. consistent with structure;
 Elemental analysis for $C_{24}H_{28}N_4O_6$: Theory: C, 61.53; H, 6.02; N, 11.96; Found: C, 61.59; H, 6.02; N, 11.93.

EXAMPLE 57

5-[4-(4-Acetyl-3-hydroxy-2-(n-propyl)phenoxy)butyl]-2H-tetrazole-2-[4-(methylene)3-hydroxybenzoic acid]

In a manner similar to that of Example 44, the title carboxylic acid was obtained from the corresponding ethyl ester using the following reaction conditions:
5-[4-(4-acetyl-3-hydroxy-2-(n-propyl)phenoxy)butyl]-2H-tetrazole-2-(ethyl 4-methylene-3-acetoxybenzoate): (4.0 g, 7.4 mmol)
4N KOH: (15 ml)
Absolute ethanol: (150 ml)
Stir time: 27 hours
Acidification, 6N HCl: (11 ml, 2.5 pH)
*Partition:
 Water: (50 ml)
 Ethyl acetate: (150 ml)
*(Enough water was first added to acidified mixture to effect solution, and the solution was concentrated)
Crystallization:
 (a) Preparatory-scale HPLC; silica gel column:
 (1) gradient: 1:3 EA:hexane plus 1% acetic acid (4 l) to 1:1 EA:hexane plus 1% acetic acid (4 l);
 (b) recrystallized from EA/hexane
 Yield: 1.29 g (37%)
 m.p.: 157–159
 n.m.r. consistent with structure;
 Elemental analysis for $C_{24}H_{28}N_4O_6$: Theory: C, 61.53; H, 6.02; N, 11.96; Found: C, 61.66; H, 6.06; N, 11.86.

EXAMPLE 58

5-[Para-(4-Acetyl-3-hydroxy-2-(n-propyl)phenoxy)-phenyl]-2H-tetrazole-2-[para(methylene)benzoic acid]

In a procedure similar to Example 25, the carboxylic acid title compound was made using the following reaction conditions:
5-[para-(4-acetyl-3-hydroxy-2-(n-propyl)phenoxy)-phenyl]-2-[para-(methylene)benzonitrile]-2H-tetrazole: (0.28 g, 0.62 mmol)
Absolute ethanol: (2 ml)
2.5N NaOH: (10 ml)

Reflux time: overnight
6N HCl: (5 ml)
Ethyl acetate (extraction): (35 ml)
Flash Chromatrography:
Column: (Kieselgel ® 60, 230-400 mesh, 2 cm×15 cm length)
Eluant: (Isocratic): 1:1 EA:hexane plus 1% HOAc
Crystallization: ether/hexane (then dried in vacuo overnight)
  Yield: 0.11 g (38%)
  m.p.: 137°-142° C.
  n.m.r. consistent with structure;
  Elemental Analysis for $C_{26}H_{24}N_4O_5$: Theory: C, 66.09; H, 5.12; N, 11.86; Found: C, 66.31; H, 5.26; N, 11.81.

EXAMPLE 59

5-[4-(4-Acetyl-3-hydroxy-2-(n-propyl)phenoxy)butyl]-2-[5-(1H-tetrazol-5-yl)propyl]-2H-tetrazole.

In a manner similar to Example 25, the title compound was prepared using the following reaction conditions:
5-[para-(4-acetyl-3-hydroxy-2-(n-propyl)phenoxy)phenyl-2-[3-(cyano)propyl]-2H-tetrazole (0.60 g, 1.5 mmol)
Tris(n-butyl)tin azide: (2.0 ml, 7.5 mmol)
DME: (5.0 ml)
Reflux time: 42 hours
Methanol: (20 ml)
1N HCl: (8 ml)
Stir time, temperature: room temperature for 1 hour.
Flash Chromatography: (Kieselgel ® 60, 230-400 mesh, 4 cm×15 cm length): *eluted with a step gradient:
  (1) 30% EA/Hexane (1 l);
  (2) 40% EA/Hexane (0.5 l);
  (3) 50% EA/Hexane (0.5 l);
  (4) 60% EA/Hexane (0.5 l);
  (5) 70% EA/Hexane (0.5 l);
*(Each mixture in the gradient step contained 1% HOAc)
Crystallization: concentrate (oil) dissolved in EA/hexane, taken to foam. After 48 hrs, crystallization began, all solid recrystallized from EA/hexane
  Yield: 0.22 g, (33%)
  n.m.r. consistent with structure;
  Elemental Analysis for $C_{22}H_{24}N_8O_3$: Theory: C, 58.92; H, 5.39; N, 24.99; Found: C, 58.66; H, 5.46; N, 24.90.

EXAMPLE 60

5-[para-(4-Acetyl-3-hydroxy-2-(n-propyl)phenoxy)-phenyl]-2H-tetrazole-2-[4-butanoic acid]

In a procedure similar to Example 29, the carboxylic acid title compound was made using the following reaction conditions:
5-[para-(4-acetyl-3-hydroxy-2-(n-propyl)phenoxy)-phenyl]-2-[4-butyronitrile]-2H-tetrazole: (0.60 g, 1.5 mmol)
Absolute ethanol: (5 ml)
2.5N NaOH: (15 ml)
Reflux time: 26 hours
6N HCl: (6 ml, pH 2)
(The mixture was partitioned between EA (50 ml) and water (25 ml). The (separated) organic phase was washed with water (25 ml) and brine (25 ml), dried and concentrated in vacuo to an oil.
Crystallization: oil twice taken up in carbon tetrachloride and concentrated, dried in vacuo at room temperature for 1 hour. Recrystallized from ether, (stored in refrigerator overnight)
  Yield: 0.30 g, 47%
  m.p.: 129-131;
  n.m.r. consistent with structure;
  Elemental analysis for $C_{22}H_{24}N_4O_5$: Theory: C, 62.25; H, 5.70; N, 13.20; Found: C, 62.45; H, 5.91; N, 13.17.

EXAMPLE 61

5-[3-(4-Acetyl-3-hydroxy-2-(n-propyl)phenoxy) propyl]-1H-tetrazole-1-[5-pentanoic acid]

In a manner similar to that of Example 44, the title oarboxylic acid was obtained from the corresponding ethyl ester using the following reaction conditions:
Ethyl 5-[3-(4-acetyl-3-hydroxy-2-(n-propyl)phenoxy)-propyl]-1H-tetrazole-1-(5-pentanoate): (0.70 g, 1.6 mmol)
4N KOH: (3 ml)
Absolute ethanol: (25 ml)
Stir time: 2 hours
Acidification, 6N HCl: (2 ml, pH 2)
Partition:
  Water: (10 ml)
  Ethyl acetate: (30 ml)
Crystallization: from ether
  Yield: 0.37 g (57%)
  m.p. 96°-99° C.
  n.m.r. consistent with structure;
  Elemental analysis for $C_{20}H_{28}N_4O_5$: Theory: C, 59.39; H, 6.98; N, 13.85; Found: C, 59.46; H, 7.05; N, 13.72.

EXAMPLE 62

5-[3-(4-Acetyl-3-hydroxy-2-propylphenoxy)-propyl]-2H-tetrazol-2-(5-pentanoic acid)

Ethyl 5-[3-(4-acetyl-3-hydroxy-2-propylphenoxy)-propyl]-2H-tetrazol-2-(5-pentanoate) (2.30 g, 5.32 mol) absolute ethanol (75 ml), and 4N potassium hydroxide solution (10 ml) were combined and stirred at room temperature for 2 hours. The pH of the reaction solution was adjusted to approximately 2 by the addition of 6N Hydrochloric Acid (7 ml).

Elemental analysis for $C_{20}H_{20}N_4O_5$: Theory: C, 59.39; H, 6.98; N, 13.85; Found: C, 59.65; H, 6.74; N, 13.85.

The resulting mixture was filtered and the filtrate was concentrated in vacuo. The residue was partitioned between ethyl acetate (60 ml) and water (30 ml). The organic phase was washed with brine, dried over magnesium sulfate, and concentrated in vacuo to an oil which crystallized upon standing. Recrystallization of the oil from ether/hexane gave 1.55 g (72%) product as colorless crystals: m.p. 62°-64° C.

PREPARATION 1

Ethyl 4-(1H-tetrazole-5-yl)butanoate

Ethyl 4-cyanobutyrate (approximately 15 g) was dissolved in DME. Tris(n-butyl)tin azide (5 ml) was added and the reaction solution was heated to 85° overnight then cooled to room temperature. The cooled solution was diluted with methanol (20 ml) then 1N hydrochloric acid (20 ml) was added. The solution was stirred for one hour then partitioned between ethyl acetate and water. The organic layer was separated, dried over magnesium sulfate and evaporated under reduced pressure. The residue was chromatographed by preparatory-scale HPLC (silcia column) eluted with a gradient of 30 to 70% ethyl acetate in hexane plus 1% acetic and to yield 3.39 g of the title product: n.m.r.(300 MHz, CDCl$_3$) δ: 4.2 (q, 2H); 2.95 (t, 2H); 2.5 (t, 2H); 2.1 (t, 2H); 1.3 (t, 3H).

PREPARATION 2

Ethyl 4-(1H-tetrazol-5-ylmethyl)benzoate

Ethyl 4-cyanomethylbenzoate (approximately 8 g) was dissolved in DME (10 ml). The solution was added tris(n-butyl)tin azide (5 ml) and the resultant solution was stirred and heated at 85° C. overnight. The solution was cooled to room temperature. The cooled solution was diluted with methanol then acidified with 1N hydrochloric acid. The acidified mixture was stirred for one hour then partitioned between ethyl acetate and water. The organic layer was separated, dried over magnesium sulfate, filtered, and concentrated in vacuo.

The concentrate was chromatographed on a preparatory-scale HPLC (silica column) eluted with a gradient of 30 to 50% ethyl acetate in hexane plus 1% acetic acid to give 1.28 g of the title product: n.m.r. (300 MHz, CDCl$_3$) δ: 8.0 (d, 2H); 7.4 (d, 2H); 4.4 (s, 2H); 4.4 (q, 2H); 1.4 (t, 3H).

PREPARATION 3

2'-Hydroxy-3'-(n-propyl)-4'-(4-bromobutoxy)-acetophenone

2', 4'-dihydroxy-3'-(n-propyl)acetophenone (19.1 g), 1,4-dibromobutane (48 ml, 0.4 moles), potassium carbonate (13.8 g), and potassium iodide (50 mg) were combined in MEK (300 ml). The reaction mixture was stirred and heated to reflux temperature overnight then cooled to room temperature. The cooled solution was partitioned between ethyl acetate and water. The organic layer was separated, dried over magnesium sulfate, filtered and concentrated in vacuo. The concentrate was chromatographed on a preparatory-scale HPLC (silica column) eluted with a gradient of 1 to 20% ethyl acetate in hexane to yield 11.2 g of the title product: n.m.r. (300 MHz, CDCl$_3$) δ: 12.8 (s, 1H); 7.6 (d, 1H); 6.45 (d, 1H); 4.1 (t, 2H); 3.55 (t, 2H); 2.7 (t, 2H); 2.65 (s, 3H); 2.25 (m, 2H); 2.05 (m, 2H); 1.58 (m, 2H); 0.98 (t, 3H).

EXAMPLE 63

Ethyl 2-[4-(4-acetyl-3-hydroxy-2-(n-propyl)phenoxy)butyl]-2H-tetrazole-5-butanoate and the corresponding 1H-tetrazole isomer (3.3 g) 2'-Hydroxy-3'-(n-propyl)-4'-(4-bromobutoxy)acetophenone ethyl 4-(1H-tetrazol-5-yl)butanoate (1.98 g), potassium carbonate (1.4 g), potassium iodide (100 mg), and MEK (100 ml) were combined and stirred and heated to reflux temperature for 2 hours. The reaction mixture was allowed to cool to room temperature and concentrated in vacuo. The concentrate was chromatographed by preparatory-scale HPLC (silica column) eluted first with a gradient of 30% to 60% ethyl acetate in hexane plus 1% acetic acid (4 l each), then with a gradient of 60% to 100% ethyl acetate in hexane plus 1% acetic acid (2 l each). The chromatography yielded 2.4 g of the 2H-tetrazole isomer of the title product and 0.90 g of the 1H-tetrazole isomer of the title product: 2H-2tetrazole isomer: n.m.r. (300 MHz, CDCl$_3$) δ: 12.8 (s, 1H); 7.6 (d, 1H); 6.4 (d, 1H); 4.7 (t, 2H); 4.2 (q, 2H); 4.1 (t, 2H); 3.0 (t, 2H); 2.65 (t, 2H); 2.6 (s, 3H); 2.4 (t, 2H); 2.2 (m, 4H); 1.9 (m, 2H); 1.55 (m, 2H); 1.3 (t, 3H); 0.98 (t, 3H).

1H-1-tetrazole isomer: n.m.r. (300 MHz, CDCl$_3$) δ: 12.8 (s, 1H); 7.6 (d, 1H); 6.4 (d, 1H); 4.4 (t, 2H); 4.1 (m, 4H); 3.0 (t, 2H); 2.65 (t, 2H); 2.6 (s, 3H); 2.5 (t, 2H); 2.2 (m, 4H); 1.9 (m, 2H); 1.55 (m, 2H); 1.3 (t, 3H); 0.97 (t, 3H).

EXAMPLE 64

2-[4-(4-Acetyl-3-hydroxy-2-(n-propyl)phenoxy)-butyl]-2H-tetrazole-5-butanoic acid Ethyl 2-[4-(4-acetyl-3-hydroxy-2-(n-propyl) phenoxy)butyl]-2H-tetrazole-5-butanoate (2.4 g) was combined with 5N potassium hydroxide solution (20 ml) in absolute ethanol (20 ml). The mixture was heated to 50° C. for 0.5 hours then cooled to room temperature. The cooled mixture was partitioned between ethyl acetate and water. The organic phase was separated, dried over magnesium sulfate, filtered, and concentrated in vacuo. The concentrate was chromatographed by preparatory-scale HPLC (silica column) eluted with a gradient of 25% to 50% ethyl acetate in hexane plus 1% acetic acid to yield the title product: n.m.r. (300 MHz, CDCl$_3$) δ: 12.80 (s, 1H); 7.54 (d, 1H); 6.35 (d, 1H); 4.60 (t, 2H); 4.01 (t, 2H); 2.82 (m, 2H); 2.57 (t, 2H); 2.51 (s, 3H); 2.20 (m, 4H); 1.95 (m, 2H); 1.80 (m, 2H); 1.46 (m, 2H); 0.88 (t, 3H).

EXAMPLE 65

1-4-(4-acetyl-3-hydroxy-2-(n-propylphenoxy)butyl]-1H-tetrazole-5-butanoic acid

Ethyl 1-[4-(4-acetyl-3-hydroxy-2-(n-propyl) phenoxy)butyl]-1H-tetrazole-5-butanoate (900 mg) was combined with 5N potassium hydroxide (20 ml) and absolute ethanol (10 ml). The solution mixture was heated to 50° C. for 0.5 hours then cooled to room temperature. The cooled solution was partitioned between water and ethyl acetate. The aqueous layer was separated and its pH was adjusted to 2.5 by the addition of 1N HCl. The acidified aqueous layer was extracted with ethyl acetate, dried over magnesium sulfate and taken to dryness in vacuo. The residue was recrystallized from a mixture of ethyl acetate and hexane to give the title product: n.m.r (300 MHz, CDCl$_3$): 12.75 (s, 1H); 7.60 (d, 1H); 6.42 (d, 1H); 4.39 (t, 2H); 4.09 (t, 2H); 2.96 (s, 3H); 2.55 (t, 2H); 2.16 (m, 4H); 1.90 (m, 2H); 1.53 (m, 2H); 0.92 (t,3H);

Analysis Calculated for C$_{20}$H$_{28}$H$_4$O$_5$: Theory: C, 59.39; H, 6.98; N, 13.85; Found: C, 59.16; H, 6.95; N, 13.58.

EXAMPLE 66

Ethyl 4-[[2-[4-(4-acetyl-3-hydroxy-2-(n-propyl) phenoxy)-2H-tetrazol-5-yl]methyl]benzoate, and the corresponding 1H-isomer 2'-Hydroxy-3'-(n-propyl)-4'-(bromobutoxy)acetophenone (1.65 g, 5 mmol), ethyl 4-(1H-tetrazol-5ylmethyl)-benzoate (1.16 g, 5 mmol), potassium iodide (50 mg), potassium carbonate (64 g), and MEK (200 ml) were combined then stirred and heated at reflux temperature for 2 hours. The reaction mixture was cooled to room temperature then partitioned between ethyl acetate and water. The organic layer was separated, dried over magnesium sulfate, filtered and concentrated in vacuo. The concentrate was chromatographed by preparatory-scale HPLC (silicia column) eluted with a gradient of 20% to 40% ethyl acetate in hexane to yield 1.3 g of 2H-tetrazole isomer of the title product: n.m.r. (300 MHz, CDCl$_3$) δ: 12.8 (s, 1H); 8.0 (d, 2H); 7.6 (d, 1H); 7.4 (d, 2H); 6.4 (d, 1H); 4.8 (t, 2H); 4.4 (q, 2H); 4.35 (s, 2H); 4.1 (t, 2H); 2.65 (t, 2H); 2.6 (s, 3H); 2.3 (m, 2H); 1.9 (m, 2H); 1.6 (m, 2H); 1.4 (t, 3H); and 0.95 (t, 3H); and 280 mg of 1H-tetrazole isomer of the title product: n.m.r. (300 MHz, CDCl$_3$) δ: 12.8 (s, 1H); 8.0 (d, 2H); 7.6 (d, 1H); 7.3 (d, 2H); 6.4 (d, 1H); 4.4 (t, 2H); 4.4 (q, 2H); 4.35 (s, 2H); 4.1 (t, 2H); 2.65 (t, 2H); 2.6 (s, 3H); 2.3 (m, 2H); 2.0 (m, 2H); 1.8 (m, 2H); 1.4 (t, 3H); 0.9 (t, 3H).

EXAMPLE 67

4-[[2-[4-(4-Acetyl-3-hydroxy-2-(n-propyl)phenoxy)-butyl]-2H-tetrazol-5-yl]methyl]benzoic acid Ethyl 4-[2-[4-(4-acetyl-3-hydroxy-2-(n-propyl)-phenoxy)butyl]-2H-tetrazole-5-yl]methyl]benzoate (1.3 g) was combined with 5N potassium hydroxide solution (20 ml) in absolute ethanol (10 ml) and the solution was heated to 60° C. for 0.5 hours. The solution was cooled to room temperature. The cooled solution was partitioned between ethyl acetate and water. The water layer was separated and its pH was adjusted to 2.5 by the addition of 1N HCl. The acidified aqueous layer was extracted with ethyl acetate. The extract was dried over magnesium sulfate, filtered, and concentrated in vacuo. The concentrate was recrystallized from ether to yield the product: n.m.r. (300 MHz, CDCl$_3$) δ: 12.79 (s, 1H); 8.06 (d, 2H); 7.59 (d, 1H); 7.43 (d, 2H); 6.40 (d, 1H); 4.70 (t, 2H); 4.33 (s, 2H); 4.06 (t, 2H); 2.63 (t, 2H); 2.58 (s, 3H); 2.25 (m, 2H); 1.86 (m, 2H); 1.54 (m, 2H); 0.93 (t, 3H).

Analysis for $C_{24}H_{28}N_4O_5$: Theory: C, 63.70; H, 6.24; N, 12.38; Found: C, 63.72; H, 6.35; N, 12.10.

EXAMPLE 68

4-[[1-4-(4-Acetyl-3-hydroxy-2-(n-propyl)phenoxy)-butyl]-1H-tetrazol-5-yl]methyl]benzoic acid In a manner similar to Example 67, the following reagents and starting materials were reacted:
Ethyl 4-[[1-[4-(4-acetyl-3-hydroxy-2-(n-propyl)phenoxy)butyl]-1H-tetrazol-5-yl]methyl]benzoate (280 mg);
5N KOH: (5 ml);
Absolute ethanol: (5 ml);
(stirred at 50° C. for 0.5 hours).

The cooled reaction solution was partitioned between ethyl acetate and water. The aqueous layer was acidified with 1N hydrochloric acid, washed with water, dried and evaporated to dryness. The residue was recrystallized from ether to yield 85 mg of the title product: m.p. 99°-102° C.; n.m.r (300 MHz, CDCl$_3$): 12.77 (s, 1H); 8.05 (d, 2H); 7.60 (d, 1H); 7.30 (d, 2H); 6.35 (d, 1H); 4.39 (s, 2H); 4.26 (t, 2H); 3.94 (t, 2H);2.59 (t, 2H); 2.57 (s, 3H); 1.99 (m, 2H); 1.76 (m, 2H); 1.52 (m, 2H); 0.91 (t, 3H).

Analysis Calculated for $C_{24}H_{28}N_4O_5$: Theory: C, 63.70; H, 6.24; N, 12.38; Found: C, 63.64; H, 6.23; N, 11.94.

EXAMPLE 69

5-[4-(4-Acetyl-3-hydroxy-2-propylphenoxy)butyl]-2H-tetrazole-2-(α-(p-methylenebenzoic acid)), sodium salt 5-[4-(4-Acetyl-3-hydroxy-2-propylphenoxy)butyl]-2H-tetrazole-2-(α-(p-methylene-p-benzoic acid)) (9.05 g, 20.0 mmol) absolute ethanol (200 ml), and 5N sodium hydroxide (4.0 ml, 20 mmol) were combined and stirred for 20 minutes at room temperature then concentrated under reduced pressure. The resulting foam was stirred in ether at room temperature overnight. The white solid thus obtained was collected by suction filtration and dried in vacuo at 35° C. overnight to yield 8.4 g, (89%) of the title product: m.p.: 215° C. (dec.); n.m.r. (300 MHz, DMSO-d$_6$) δ: 12.81 (s, 1H); 7.82 (d, 2H); 7.76 (d, 1H); 7.20 (d, 2H); 6.59 d, 1H); 5.83 (s, 2H); 4.08 (t, 2H); 2.89 (t, 2H); 2.55 (s, 3H); 1.82 (m, 4H); 1.41 (m, 2H); 0.81 (t, 3H).

Analysis Calculated for $C_{24}H_{27}N_4O_5$: Theory: C, 60.75; H, 5.74; N, 11.81; Found: C, 60.69; H, 5.65; N, 11.90.

EXAMPLE 70

5-[4-(4-Acetyl-3-hydroxy-2-(n-propyl)phenoxy)butyl]-2-4-(1H-tetrazole-5-yl)butyl]-2H-tetrazole, sodium salt 5-[4-(4-Acetyl-3-hydroxy-2-(n-propyl)phenoxy)-butyl]-2-4-(1H-tetrazole-5-yl)butyl]-2H-tetrazole, (0.88 g, 2.0 mmol) was suspended in absolute ethanol (10 ml), and 5N sodium hydroxide solution (0.40 ml) was added in a dropwise fashion. The solution was stirred for 15 minutes at room temperature then concentrated in vacuo. Ethanol was added to the concentrate which was again concentrated. The resultant oil was dried in vacuo to produce a foam. The foam was dried overnight in vacuo to yield 0.60 g, 65% of the title product: n.m.r. (300 MHz, DMSO-d$_6$) δ: 12.81 (s, 1H); 7.78 (d, 1H); 6.61 (d, 1H); 4.60 (t, 2h); 4.11 (t, 2H); 2.90 (t, 2H); 2.62 (t, 2H); 2.56 (s, 3H); 2.50 (m, 2H, partially obscured by DMSO peak at 2.49); 1.86 (m, 6H); 1.54 (m, 2H); 1.44 (m, 2H); 0.85 (t, 3H).

Analysis Calculated for $C_{21}H_{29}N_8O_3Na\cdot\frac{1}{2}H_2O$: Theory: C, 53.27; H, 6.39; N, 23.66; Found: C, 53.22; H, 6.29; N, 23.67.

EXAMPLE 71

Hard gelatin capsules are prepared using the following ingredients:

| | Quantity (mg/capsule) |
|---|---|
| 5-[4-(4-Acetyl-3-hydroxy-2-(n-propyl)phenoxy)butyl]-2-[4-(1H—tetrazol-5-yl)butyl]-2H—tetrazole | 250 |
| Starch | 200 |
| Magnesium stearate | 10 |

The above ingredients are mixed and filled into hard gelatin capsules in 460 mg quantities.

EXAMPLE 72

A tablet is prepared using the ingredients below:

| | Quantity (mg/tablet) |
|---|---|
| 5-[4-(4-Acetyl-3-hydroxy-2-(n-propyl)phenoxy)butyl]-2-[4-(1H—tetrazol-5-yl]butyl]-2H—tetrazole, sodium salt | 250 |
| Cellulose, microcrystalline | 400 |
| Silicon dioxide, fumed | 10 |
| Magnesium stearate | 5 |

The components are blended and compressed to form tablets each weighing 665 mg.

EXAMPLE 73

An aerosol solution is prepared containing the following components:

| | Weight % |
|---|---|
| 5-[4-(4-Acetyl-3-hydroxy-2-(n-propyl)phenoxy)butyl]-2H—tetrazole-2-(α-(p-methylenebenzoic acid)) sodium salt | 0.25 |
| Ethanol | 30.00 |
| Propellant 11 (trichlorofluoromethane) | 10.25 |
| Propellant 12 (Dichlorodifluoromethane) | 29.75 |
| Propellant 114 (Dichlorotetrafluoroethane) | 29.75 |

The active compound is dissolved in the ethanol and the solution is added to the propellant 11, cooled to −30° C. and transferred to a filling device. The required amount is then fed to a container and further filled with the pre-mixed propellants 12 and 114 by means of the cold-filled method or pressure-filled method. The valve units are then fitted to the container.

EXAMPLE 74

Tablets each containing 60 mg of active ingredient are made up as follows:

| | |
|---|---|
| 5-[4-(4-Acetyl-3-hydroxy-2-propyl-phenoxy)butyl]-2H—tetrazole-2-(α-(p-methylenebenzoic acid)), sodium salt | 60 mg |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°-60° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

EXAMPLE 75

Capsules each containing 80 mg of medicament are made as follows:

| | |
|---|---|
| 5-[4-(4-Acetyl-3-hydroxy-2-(n-propyl)-phenoxy)butyl]-2-[4-(1H—tetrazol-5-yl)butyl]-2H—tetrazole | 80 mg |
| Starch | 59 mg |
| Microcrystalline cellulose | 59 mg |
| Magnesium stearate | 2 mg |
| Total | 200 mg |

The active ingredient, cellulose, strarch and magnesium stearate are blended, passed through a No. 45 mesh U.S. sieve, and filled into hard gelatin capsules in 200 mg quantities.

EXAMPLE 76

Suppositories each containing 225 mg of active ingredient are made as follows:

| | |
|---|---|
| 5-[4-(4-Acetyl-3-hydroxy-2-propyl-phenoxy)butyl]-2H—tetrazol-2-(4-butyric acid) | 225 mg |
| Unsaturated or saturated fatty acid glycerides to | 2,000 mg |

The active ingredient is passed through a No. 60 mesh U.S. sieve and suspended in the fatty acid glycerides previously melted using the minimum heat necessary. The mixture is then poured into a suppository mold of nominal 2 g capacity and allowed to cool.

EXAMPLE 77

Suspensions each containing 50 mg of medicament per 5 ml dose are made as follows:

| | |
|---|---|
| 5-[4-(4-Acetyl-3-hydroxy-2-(n-propyl)phenoxy)butyl]-2-[4-(1H—tetrazol-5-yl)butyl]-2H—tetrazole | 50 mg |
| Sodium carboxymethyl cellulose | 50 mg |
| Sugar | 1 g |
| Methyl paraben | 0.05 mg |
| Propyl paraben | 0.03 mg |
| Flavor | q.v. |
| Color | q.v. |
| Purified water to | 5 ml |

The medicament is passed through a No. 45 mesh U.S. sieve and mixed with the sodium carboxymethylcellulose, sugar, and a portion of the water to form a suspension. The parabens, flavor and color are dissolved and diluted with some of the water and added, with stirring. Sufficient water is then added to produce the required volume.

We claim:

1. A compound of the formula

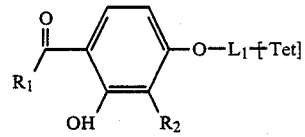

wherein:
$R_1$ is $C_1$ to $C_8$ alkyl or phenyl;
$R_2$ is $C_2$ to $C_8$ alkyl or $C_3$ to $C_8$ alkenyl;
$L_1$ is $C_4$ alkylidene or phenyl;
[Tet] is a disubstituted 2H-tetrazolyl ring of the formula:

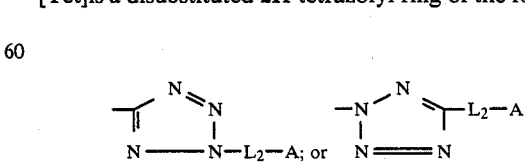

$L_2$ is
(1) a $C_2$ to $C_{10}$ alkylidene group; or
(2) a benzyl group of the formula:

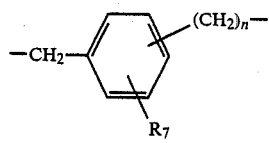

wherein $R_7$ is a hydrogen atom, hydroxy group, or acetoxy; and n is from 0 to 3; (and the single methylene group bonded to the ring is also bonded to the tetrazolyl ring [Tet]);

A is
(1) a group of the formula —COOH; or
(2) a 5-(tetrazolyl) group; with the proviso that when $L_1$ is phenyl, —$L_2$—A cannot be bonded to the five position of [Tet] tetrazolyl ring;

or a phamaceutically-acceptable salt thereof.

2. A compound of claim 1, wherein $R_1$ is methyl and $R_2$ is n-propyl.

3. A compound of claim 2, wherein $L_1$ and [Tet] together give a group of the formula

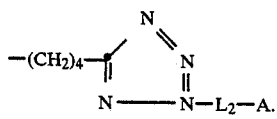

4. A compound of claim 3, wherein $L_2$ is (a) n-($C_2$ to $C_6$) alkylitene or b) a group of the formula

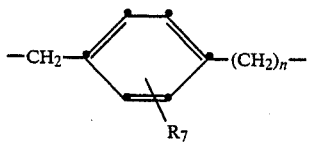

wherein n is 0 or 1.

5. A compound of claim 4, wherein A is 5-(tetrazolyl) and $L_2$ is n-($C_2$ to $C_5$)alkylidene.

6. A compound of claim 5, wherein $L_2$ is $CH_2CH_2CH_2CH_2$.

7. A compound of claim 6, which comprises the sodium salt thereof.

8. A compound of claim 5, wherein $L_2$ is $CH_2CH_2CH_2$.

9. A compound of claim 4, wherein A is a group of the formula —COOH and $L_2$ is n-($C_2$ to $C_5$)alkyledene.

10. A compound of claim 9, wherein $L_2$ is $CH_2CH_2CH_2$.

11. A compound of claim 9, wherein $L_2$ is $CH_2CH_2CH_2CH_2CH_2$.

12. A compound of claim 4, wherein A is a group of the formula —COOH and $L_2$ is a group of the formula

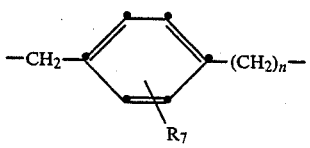

wherein n is 0 or 1 and $R_7$ is a hydrogen atom.

13. A compound of claim 12, wherein $R_7$ and A together form a para-(methylene)benzoic acid moiety.

14. A compound of claim 13, which comprises the sodium salt thereof.

15. A compound of claim 2, wherein $L_1$ and [Tet] taken together form a group of the formula

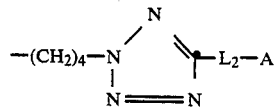

16. A compound of claim 15 wherein $L_2$ is n-($C_2$ to $C_5$)alkylidene or a benzyl group of the formula

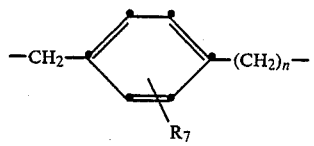

wherein n is 0 or 1 and $R_7$ is a hydrogen atom.

17. A compound of claim 16, wherein A is a group of the formula —COOH and $L_2$ is $CH_2CH_2CH_2$.

18. A compound of claim 16, wherein $L_2$ and A taken together form a para-(methylene)benzoic acid substituent.

19. A compound of the formula

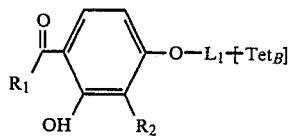

wherein:
$R_1$ is $C_1$ to $C_8$ alkyl or phenyl;
$R_2$ is $C_2$ to $C_8$ alkyl or $C_3$ to $C_6$ alkenyl;
$L_1$ is $C_4$ alkylidene or phenyl;
[$Tet_B$] to is a disubstituted 2H-tetrazolyl ring of the formula:

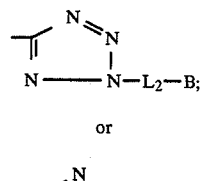

or

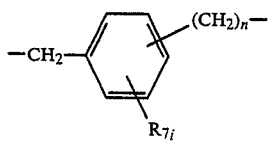

wherein:
$L_2$ is
(1) a $C_2$ to $C_{10}$ alkylidene group; or
(2) a benzyl group of the formula:

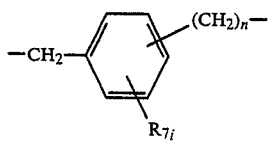

wherein $R_{7i}$ is an acetoxy group or a protected hydroxy group, and n is from 0 to 3; (and the single methylene group is also bonded [Tet$_B$]) and B is
(1) a group of the formula

—COOR$_8$ wherein R$_8$ is ethyl or a carboxy-protecting group;
(2) cyano; or
(3) halo; with the proviso that, when L$_1$ is phenyl, —L$_2$—B is not bonded to the 5-position of the [Tet$_B$] tetrazolyl ring.

20. A compound of claim 19, wherein R$_1$ is methyl and R$_2$ is n-propyl.

21. A compound of claim 20, wherein L$_1$ and [Tet$_B$] taken together give a group of the formula

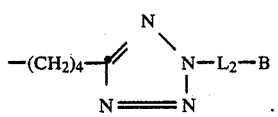

22. A compound of claim 21, wherein
(a) B is cyano and L$_2$ is n-(C$_2$ to C$_6$)alkylidene or a benzyl group of the formula

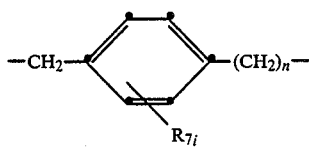

wherein
n is 0 or 1; and
R$_{7i}$ is hydrogen;
(b) B is an ethyl ester moiety and L$_2$ is (1) n-(C$_2$ to C$_5$) alkyledene or (2) a benzyl group of the formula

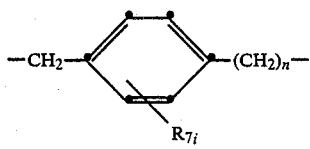

wherein R$_{7i}$ is ortho- or meta-acetoxy and n is 0 or
(c) B is bromo and L$_2$ is a benzyl group of the formula

23. A compound of claim 22, wherein B is cyano and L$_2$ is n-(C$_2$ to C$_5$)alkylidene or a benzyl group of the formula

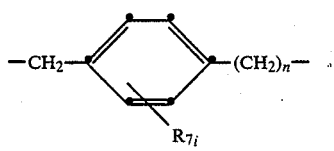

wherein R$_{7i}$ is a hydrogen atom and n is 0 or 1.

24. A compound of claim 23, wherein L$_2$ is CH$_2$CH$_2$CH$_2$CH$_2$.

25. A compound of claim 22, wherein L$_2$ and B taken together form an meta- or para-(methylene)benzonitrile substituent.

26. A compound of claim 20, wherein L$_1$ and [Tet$_B$] taken together give a group of the formula:

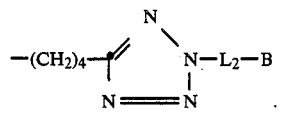

27. A compound of claim 26, wherein B is an ethyl ester moiety and L$_2$ is (1) n-(C$_2$ to C$_5$)alkylidene; or (2) a benzyl group of the formula

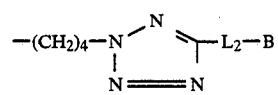

wherein R$_{7i}$ is hydrogen and n is 0 or 1.

28. A compound of claim 27 wherein L$_2$ is CH$_2$CH$_2$CH$_2$ or a para-substituted benzyl group (n=0).

29. A pharmaceutical formulation, which comprises a therapeutically-effective amount of a compound of claim 1 and a pharmaceutically-acceptable carrier.

30. A pharmaceutcal formulation, which comprises a therapeutically-effective amount of a compound of claim 3 and a pharmaceutically-acceptable carrier.

31. A pharmaceutical formulation, which comprises a therapeutically-effective amount of a compound of claim 6 and a pharmaceutically-acceptable carrier.

32. A pharmaceutical formulation, which comprises a therapeutically-effective amount of the compound of claim 7 and a pharmaceutically-acceptable carrier.

33. A method of treating a mammal suffering from or susceptible to any condition characterized by an excessive release of either leukotriene C$_4$, D$_4$, or E$_4$ or any combination thereof, which comprises administering to said mammal a leukotriene antagonizing amount of a compound of claim 1.

34. A method of treating a mammal suffering from or susceptible to any condition characterized by an excessive release of either leukotriene C$_4$, D$_4$, or E$_4$ or any combination thereof, which comprises administering to said mammal a leukotriene antagonizing amount of a compound of claim 3.

35. A method of treating a mammal suffering from or susceptible to any condition characterized by an excessive release of either leukotriene C$_4$, D$_4$, or E$_4$, or any combination thereof, which comprises adminstering to said mammal a leukotriene antagonizing amount of a compound of claim 6.

36. A method of treating a mammal suffering from or susceptible to any condition characterized by an excessive release of leukotriene C$_4$, D$_4$, or E$_4$ or any combination thereof, which comprises administering to said mammal a leukotriene antagonizing amount of a compound of claim 7.

37. A method of treating a mammal suffering from or susceptible to an immediate hypersensitivity reaction of the type represented by asthma, which comprises administering to said mammal a therapeutically-effective amount of a compound of claim 1.

38. A method of treating a mammal suffering from or susceptible to an immediate hypersensitivity reaction of the type represented by asthma, which comprises administering to said mammal a therapeutically-effective amount of a compound of claim 3.

39. A method of treating a mammal suffering from or susceptible to an immediate hypersensitivity reaction of the type represented by asthma, which comprises administering to said mammal a therapeutically-effective amount of a compound of claim 6.

40. A method of treating a mammal suffering from or susceptible to an immediate hypersensitivity reaction of the type represented by asthma, which comprises administering to said mammal a therapeutically-effective amount of a compound of claim 7.

41. A method of treating a mammal suffering from or susceptible to shock or other adverse cardiovascular effects of excessive release or production of either leukotriene $C_4$, $D_4$, or $E_4$ or any combination thereof, which comprises administering to said mammal a leukotriene antagonizing amount of a compound of claim 1.

42. A method of treating a mammal suffering from or susceptible to shock or other adverse cardiovascular effects of excessive release or production of either leukotriene $C_4$, $D_4$, or $E_4$, or any combination thereof, which comprises administering to said mammal a leukotriene antagonizing amount of a compound of claim 3.

* * * * *